United States Patent
Nekoui et al.

(10) Patent No.: US 9,019,948 B2
(45) Date of Patent: Apr. 28, 2015

(54) ALLOCATION SLOT ARRANGEMENT FOR WIRELESS BODY AREA NETWORKS WITH SENSOR INITIATED GRANT EXTENSIONS

(71) Applicant: Olympus Corporation, Tokyo (JP)

(72) Inventors: Mohammad Nekoui, San Diego, CA (US); Rongsheng Huang, San Diego, CA (US); Lichung Chu, San Diego, CA (US)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/918,954

(22) Filed: Jun. 15, 2013

(65) Prior Publication Data

US 2014/0369339 A1     Dec. 18, 2014

(51) Int. Cl.
    *H04B 7/212*     (2006.01)
    *H04W 4/00*     (2009.01)
    *H04W 74/04*     (2009.01)

(52) U.S. Cl.
    CPC .................................. *H04W 74/04* (2013.01)

(58) Field of Classification Search
None
See application file for complete search history.

(56) References Cited

U.S. PATENT DOCUMENTS

| | | | |
|---|---|---|---|
| 8,055,763 B2* | 11/2011 | Yoo et al. | 709/224 |
| 2007/0230501 A1* | 10/2007 | Bibby et al. | 370/468 |
| 2008/0144493 A1* | 6/2008 | Yeh | 370/230 |
| 2009/0067389 A1* | 3/2009 | Lee et al. | 370/336 |
| 2012/0082036 A1* | 4/2012 | Abedi et al. | 370/241 |
| 2012/0119902 A1* | 5/2012 | Patro et al. | 340/502 |
| 2013/0343360 A1* | 12/2013 | Poovendran et al. | 370/336 |

\* cited by examiner

*Primary Examiner* — Edan Orgad
*Assistant Examiner* — Rebecca Song
(74) *Attorney, Agent, or Firm* — Sheppard Mullin Richter & Hampton LLP

(57) ABSTRACT

Allocation slot arrangement is provided for wireless body area networks (BANs). In particular, in some embodiments the allocation slots are arranged based on a set of rules and received input parameters. Allocation slot arrangement may comprise maximizing a weighted sum function computed by applying the rules and input parameters to all nodes over all possible arrangements.

29 Claims, 18 Drawing Sheets

| Connection ID | Connection Duration | Priority | Negotiated Allocation length | Allocation Gap | In Allocation Flag (*) | Holding Time (*) | Last Allocation (*) | Allocation Adjustment (*) |
|---|---|---|---|---|---|---|---|---|
| Connection ID allocated in connection process | (in frames) | Priority specified in connection process | (in mini slot) | (in frames) | 1 or 0 | (in frames) | (in frames) | Extra mini slots applied to this connection calculated from elastic factor or due to allocation compensation |

Fig. 6

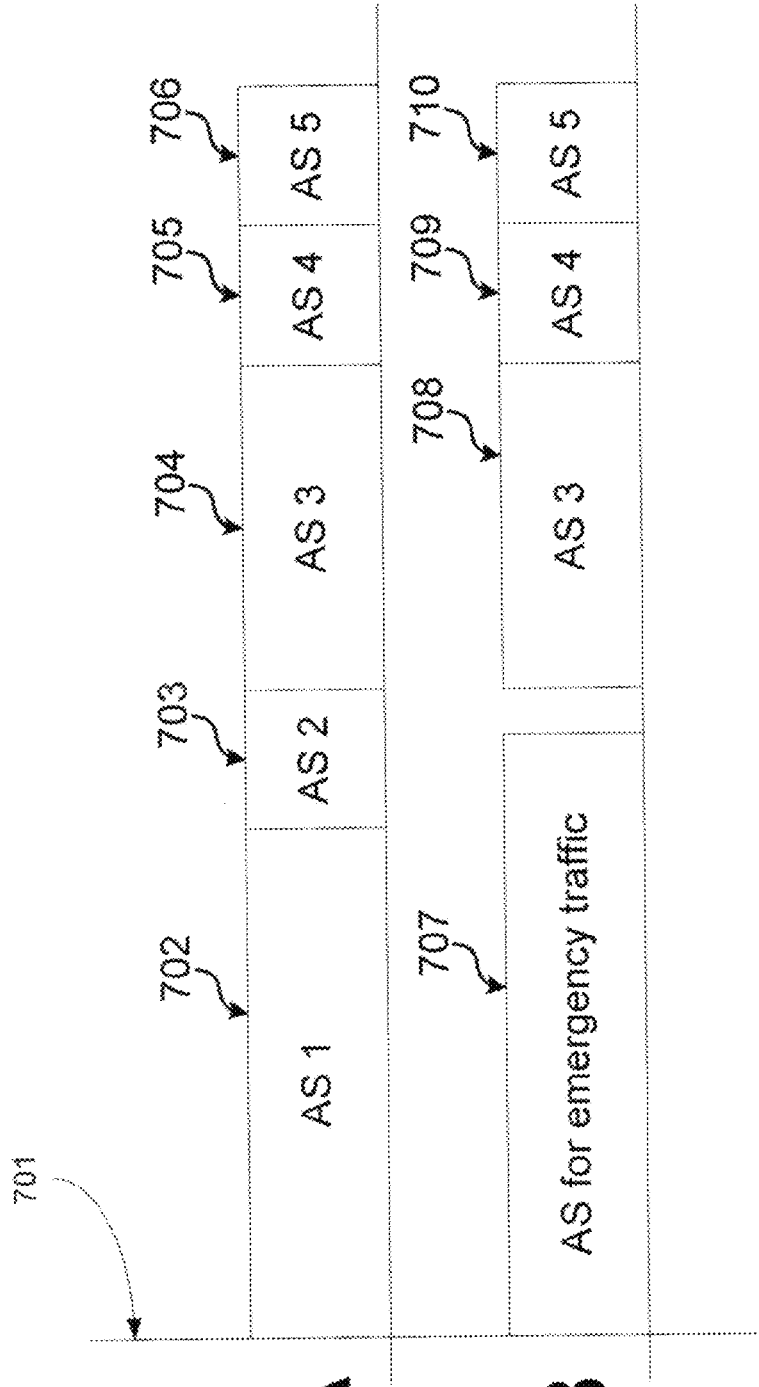

| Reserved period maximum length | | $L$ | |
|---|---|---|---|
| Emergency | Probability | $p_0$ | |
| | Distribution | $f_{\lambda_0}(x_0) \sim \exp(\lambda_0)$ | |
| | Weight factor | $w_0^n$ | |
| | Scheduled Allocation | $L_n$ | |
| | Slot length | | |
| | Reschedule Tolerance | $R_n$ | |
| | Threshold | | |
| Node n | StGE probability | $p_n$ | |
| | StGE distribution | $f_{\lambda_n}(x_n) \sim \exp(\lambda_n)$ | |

INPUT PARAMETERS

Fig. 14

ALLOCATION SLOT ARRANGEMENT FOR WIRELESS BODY AREA NETWORKS WITH SENSOR INITIATED GRANT EXTENSIONS

TECHNICAL FIELD

The disclosed technology relates generally to wireless body area networks, and more particularly, some embodiments relate to systems and methods for allocation slot arrangement for wireless body area networks with sensor initiated extensions of granted schedules.

DESCRIPTION OF THE RELATED ART

Wireless body area networks (BANs) are an emerging type of wireless network. Major targets for BANs are medical body sensors, which may be attached to or implanted in the body. Medical uses for BANs include devices that provide medical interventions, such as drug delivery devices, or pacemakers (termed "actuators").

Due to their simple star topology and power consumption limitations, BANs are typically suited for TMDA-based MAC schemes. Under this scheme, a BAN hub may negotiate connection parameters with BAN nodes. Prior to data transmission, a schedule is broadcast to all nodes indicating the allocation of slots (i.e. who is to transmit when within a reserved period). However, real-time changes in a node's requirements may necessitate changes to the prior slot allocations.

BRIEF SUMMARY OF EMBODIMENTS

Embodiments of the technology disclosed herein provide optimal allocation slot arrangement for wireless body area networks with sensor initiated extensions of granted schedules. In some embodiments, the arrangement of allocation slots for nodes depends on a set of rules that the nodes must follow in the BAN network and a set of input parameters corresponding to the nodes. The BAN can be configured to require that each BAN node can wake up only once during a reserved period. The BAN may also be configured such that allocation slots with higher Quality of Service ("QOS") priority cannot be preempted by allocation slots with lower QOS priority.

In another embodiment, arranging allocation slots depends on calculating a utility metric for each of a plurality of BAN nodes for an allocation slot arrangement, wherein the calculation of the utility metric depends on the set of rules and set of input parameters. In yet a further embodiment, arranging allocation slots additionally depends on QOS weight factors corresponding to the BAN nodes in the network.

Other features and aspects of the disclosed technology will become apparent from the following detailed description, taken in conjunction with the accompanying drawings, which illustrate, by way of example, the features in accordance with embodiments of the disclosed technology. The summary does not limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 6 illustrates an example connection table that may be maintained by the hub during BAN operation.

FIG. 7, which comprises FIGS. 7A and 7B illustrate an example of allocation slot preemption for emergency traffic during BAN operations.

FIGS. 11A, 11B, and 11C, is a diagram illustrating an example preemption mechanism.

FIG. 14 is an example set of input parameters used by the example process of FIG. 12 to arrange allocation slots.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION OF THE EMBODIMENTS

Figure 1:
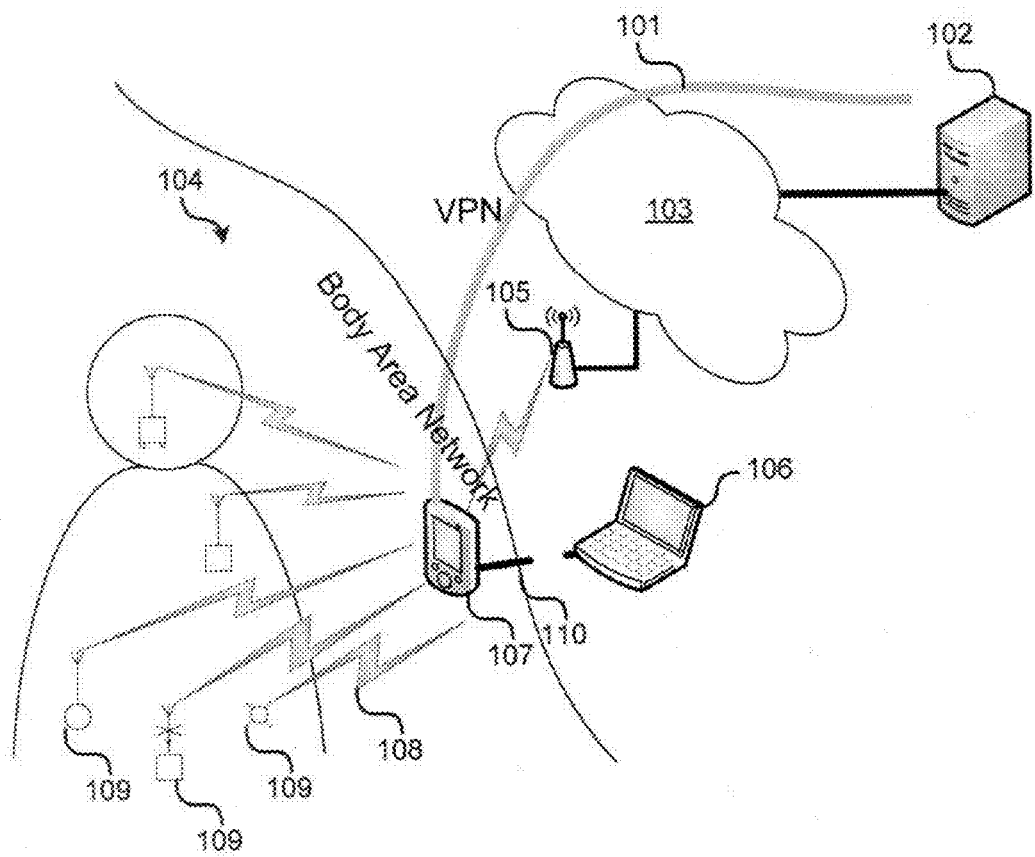
FIG. 1 illustrates an example wireless body area network (BAN).

FIG. 1 illustrates an example BAN. The BAN 104 comprises devices 109 (such as body sensors and actuators) wirelessly coupled 108 to a hub 107 in a star-topology, single-hop network. The hub 107 forms a connection 101, such as a virtual private network connection (VPN), with a trusted server 102 via a wireless access point 105, such as a wireless router or cellular tower, and a network 103, such as the Internet. For example, the hub 107 may comprise a smartphone or other personal wireless device and may connect to the access point 105 via a networking protocol such as Wi-Fi or a cellular data protocol. In some implementations, the hub 107 may form a second connection 110 to a personal computer or other personal device 106—for example, through a direct connections, such as a Bluetooth connection, or through an indirect connection, such as a wireless local area network provided by access point 105.

The trusted server 102 may comprise a remote data processing center—for example, located at a hospital—where data collected by the sensors 109 is processed or stored. The server 102 may issue certain commands to the devices 109 via hub 107. However, in typical implementations, the personal device 106 is used only to access body data and is not allowed to issue commands to the devices 109.

The devices 109 usually have a relatively low data rate (in the order of 100 kbps), low duty cycle (a few minutes of active state in one day), and relatively constant connection duration (a few minutes per connection). However, bursty traffic may be supported. Additionally, the networks 104 are usually relatively stable, with devices 109 rarely joining or leaving the network 104.

Figure 2:
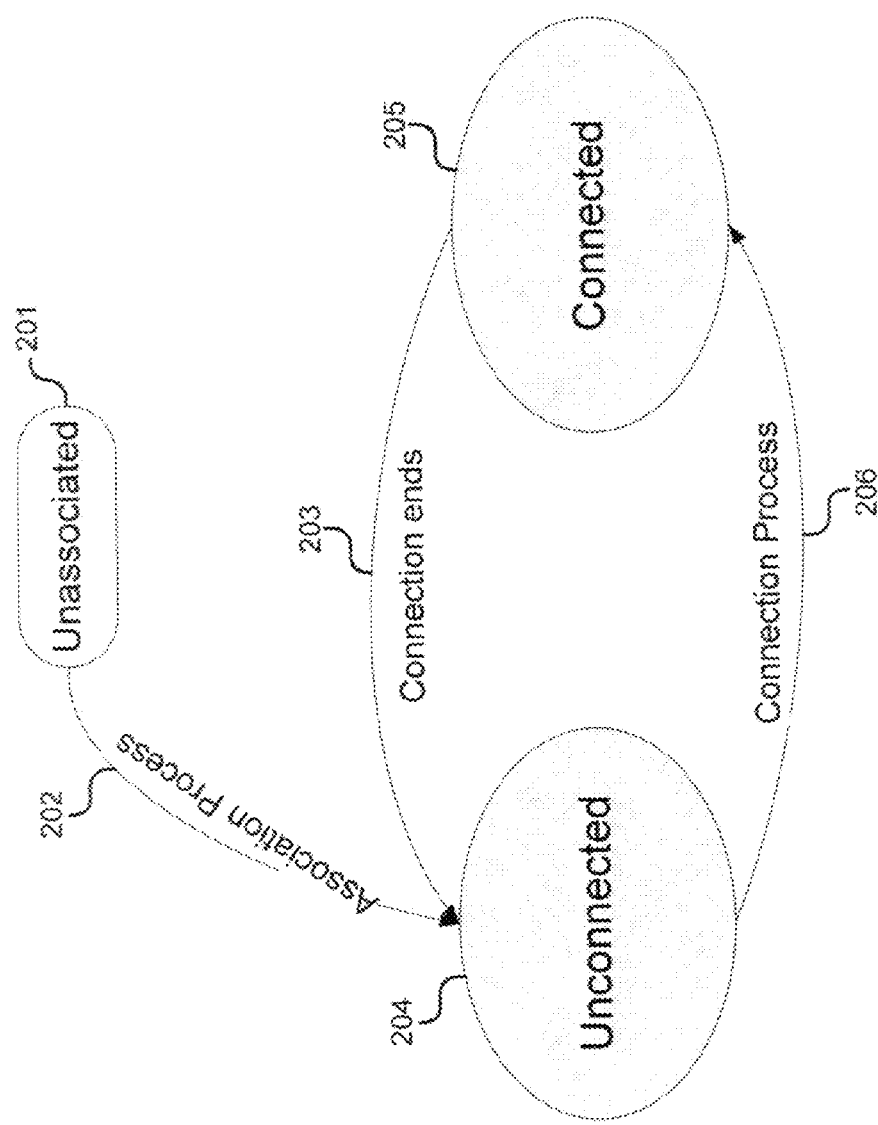
FIG. 2 illustrates various states that BAN devices may have during BAN operations.

FIG. 2 illustrates various states that BAN devices (e.g., devices 109) may have during network operations in accordance with one embodiment of the technology described herein. Each BAN device begins in an unassociated state 201. In the unassociated state 201, the BAN device is not part of the network and has not built a trust relationship with the hub or server. To join the BAN, the BAN device completes an association process 202 where the trust relationship between the hub and the BAN device is established. The association process 202 comprises transmitting an association request message from the device to the hub. Additionally, any signaling from the server required to initialize the BAN device's connection to the network can take place during the association process 202.

Additionally, devices that are able to access an emergency request period (emergency-capable devices) can register with the hub during the association process 202. Additionally, in some embodiments, emergency connection parameters are included in the association request message transmitted by the emergency-capable devices. The connection parameters set the connection requirements required to fulfill the BAN device's emergency operations. For example, if the BAN device's emergency operational requirements entail reporting bursty or continuous monitoring data to the server, the emergency connection parameters may specify the connection required to provide such reporting. The emergency connection parameters may include, for example, (a) emergency connection length requirements, (b) the size and frequency of allocations during the emergency connection, and (c) whether the emergency connection will require a continuous period of monitoring. In other cases, the BAN device may not have data to report during emergency operation—for example, the BAN device may simply issue an alarm. In these cases, the emergency connection parameters may reflect that no emergency connection is needed and that the hub should transmit an alert to the server when it receives an emergency message from the BAN device.

Once the BAN device associates with the network 202, the BAN device is in an unconnected state 204. In the unconnected state 204, the BAN device retains an association with the network, including the trust relationship with the hub. For example, once the device is in the unconnected state 204 session keys can be generated and exchanged without signaling from the server. A device in the unconnected state 204 is typically asleep. However, in some cases, the device may use an unreserved communication period (discussed below) to communicate with the hub while in the unconnected state 204. The hub assumes that a device in the unconnected state 204 is asleep, and will not schedule downlink packets for an unconnected device. Instead, if there is a downlink packet pending, the hub posts the device's ID in a wakeup list (described below).

When the device has data to transmit to the hub, it performs a connection process 206 to enter a connected state 205. For example, the device may enter the connected state 205 to transmit a sensor report to the server via the hub or to receive packets from the server via the hub. As another example, the device may enter the connected state 205 to transmit an emergency message. The connection process 206 used to enter connected state 205 may depend on whether or not the device has emergency data. The connected state 205 is the state in which a device has its transmission and reception scheduled by the hub. After the scheduled traffic has completed, the connection ends 203 and the device re-enters the unconnected state 204.

Figure 3:
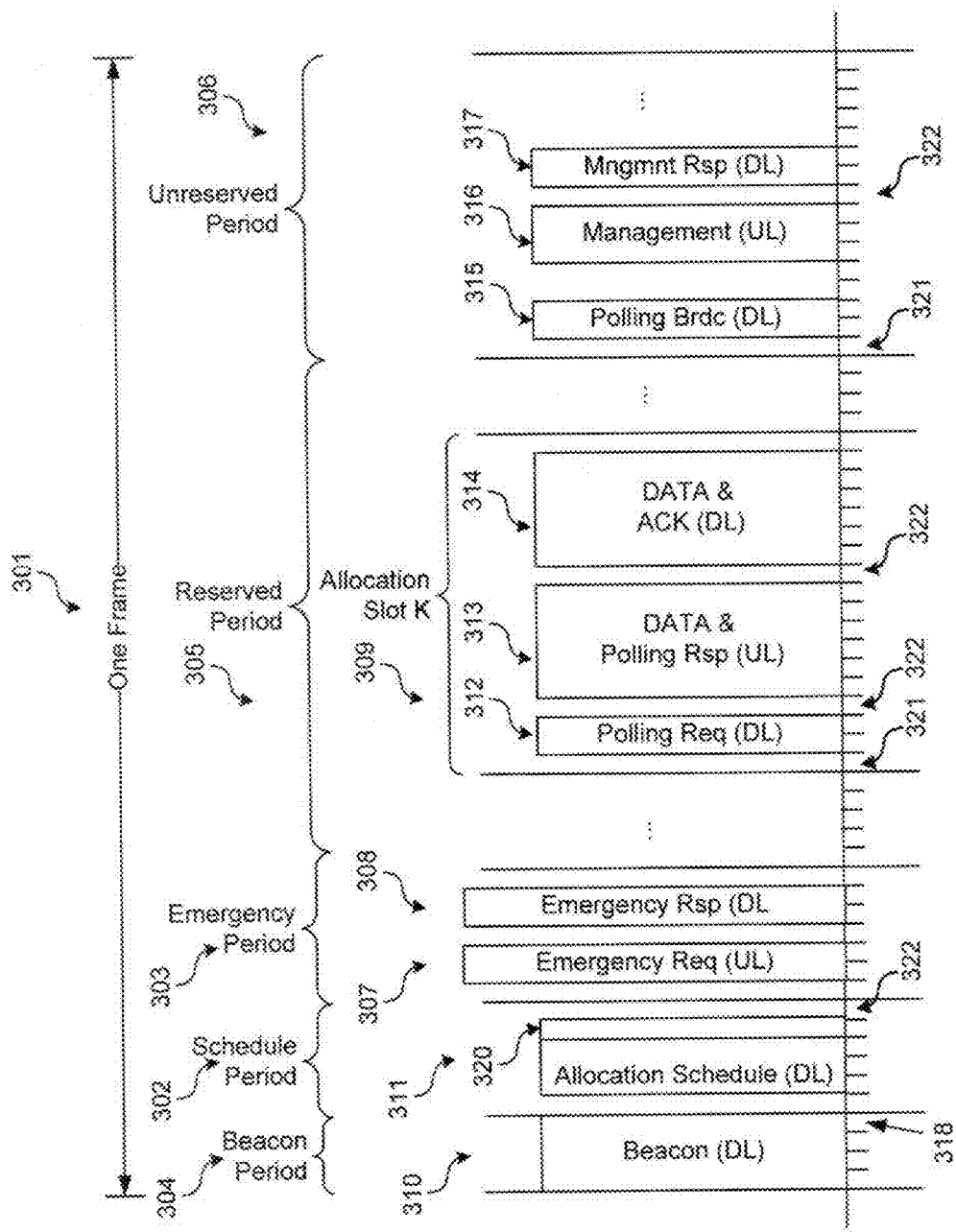
FIG. 3 illustrates an example frame structure for BAN operations.

FIG. 3 illustrates an example frame structure for use in a BAN in accordance with one embodiment of the technology described herein. Communications in some implementations utilize time-division multiple access (TDMA) for channel access in the BAN. The BAN frequency channel is divided into timeslots 318, which are grouped into frames 301. Transmissions in the frame 301 are separated by at least one short inter-frame spacing (SIFS) period 322.

The frame 301 begins with a beacon period 304 where the hub broadcasts a beacon 310. The beacon 310 may contain various information, such as, for example, (a) frame synchronization and timing information; (b) BAN information, such as the BAN ID; (c) channel information; and (d) the length of the frame.

In the illustrated example, scheduling period 302 takes place after the beacon period 304. The hub broadcasts an allocation schedule message 311 during the schedule period 302. The allocation schedule message 311 sets the division between the reserved period 305 and the unreserved period 306. The reserved period 305 is used to communicate with devices in a connected state. The unreserved period 306 is used to communicate with devices in an unconnected state and to communicate with devices in an unassociated state.

The allocation schedule message 311 can include a schedule of which BAN devices reserved allocation slots 309 during the reserved period 305. In some implementations, the allocation schedule message 311 includes the start times of all reserved allocation slots 309. This may be used by the BAN devices to determine the length of their reserved allocation slots 309. In other implementations, the allocation schedule message 311 includes the lengths of the reserved allocation slots 309. In still further implementations, the allocation slots 309 have a fixed length and the allocation schedule message 311 can include an ordered list of BAN devices. In some implementations, the allocation schedule message 311 can further includes a start time of the unreserved period 306. For example, the allocation schedule message 311 may include the start time of the unreserved period 306 if it is not calculable from the other information in the allocation schedule message 311.

The allocation schedule message 311 can further include a wake-up list 320. The wake-up list 320 comprises a list of unconnected BAN devices that have waiting downlink packets. An unconnected BAN device is listed in the wake-up list 320 in consecutive frames 301 until the BAN device builds a connection. In some implementations, the hub may have an expiration timer where an unconnected BAN is dropped from the wake-up list 320 after a certain number of frames. The wake-up list 320 allows BAN devices to remain asleep in an unconnected state for long periods. Even if a BAN device may receive unpredictable downlink traffic, there is no need for the device to check for downlink traffic every frame. Rather, the device may only check the wake-up list 320 periodically because the device will remain on the wake-up list 320 until it builds a connection.

In the illustrated example, an emergency period 303 occurs after the scheduling period 302. The BAN devices that have registered as emergency-capable during the association process 202 (FIG. 2) may use the emergency period 303. In implementations where the emergency period 303 occurs immediately after the schedule period 302, devices can access the channel immediately after listening to the beacon 310 and allocation schedule message 311. This reduces the latency need to synchronize with the hub when an emergency event occurs.

Communication during the emergency period 303 can include emergency request messages 307 transmitted by emergency-capable devices and emergency request response messages 308 transmitted by the hub. In some cases, an emergency request message 307 indicates that the hub should build a connection 206 (FIG. 2) according to the emergency connection parameters set during the association process 202 (FIG. 2). Because the emergency connection parameters can be set during association process 202 (FIG. 2), the emergency request messages 307 may be shorter than the connection request messages 316 (discussed below).

In other cases, the emergency-capable device does not need an emergency connection—for example, if the emergency-capable device simply transmits an emergency signal or short emergency data packet as the emergency request 307. In these cases, the hub may relay the emergency event to the server upon receiving the emergency request message 307. In further implementations, emergency event signaling or data packets can be included as part of the emergency request message 307 to build an emergency connection.

The emergency response 308 can be included to provide a receipt acknowledgement to the device from the hub. The emergency response 308 may also include a confirmation that the emergency connection parameters set during the association process 202 (FIG. 2) will be followed. If the emergency connection parameters will not be followed, the emergency response 308 may further include finalized values of the connection parameters. Additionally, as described below, when an emergency request 307 is transmitted, normally scheduled allocation slots 309 in the frame may be preempted to begin the emergency connection. The emergency response message 308 may include a schedule for the preempted allocation slot 309 that will be used for the first slot of the emergency connection. Allocation slots 309 during future frames of the emergency connection (i.e., frames after the one in which the emergency request 307 was transmitted) are scheduled normally and are included in the allocation schedule message 311.

The length of the emergency period 303 can be fixed by the BAN's MAC protocol. Typically, the emergency period 303 will be used only rarely. When it is not in use, the BAN can be idle. Accordingly, the length is preferably short enough to avoid unnecessary waste of channel resources. For example, the emergency period 303 may be short enough for only one, two, or three emergency request 307 and response 308 exchanges.

The access method used by the emergency-capable devices to access the emergency period 303 may differ between BANs. For example, if the number of emergency-capable devices is less or equal to the number of potential emergency request messages 307, the BAN may use a reservation-based access method. Here, the BAN may reserve specific periods within the emergency period 303 for specific emergency-capable devices.

If the number of emergency-capable devices exceeds the number of potential request messages 307, the BAN may use a contention-based access method. Here, the emergency-capable devices use a contention method to access the channel during emergency period 303. For example, the emergency-capable devices may use slotted ALOHA, carrier sense multiple access with collision avoidance (CSMA/CA), p-persistent ALOHA, or p-persistent CSMA to access the channel. Because emergency events are likely to be rare, collisions to access the channel during emergency period 303 are also likely to be rare.

In some implementations, the access method to be used is provided in the beacon 310. If the access method changes during network operation, the hub can update the beacon 310.

In still further implementations, the emergency period 303 access method is fixed. For example, contention based access may always be used to access the emergency period 303, regardless of the number of BAN devices In the illustrated example, reserved period 305 occurs after the emergency period 303. The reserved period 305 can include one or more allocation slots 309. Each allocation slot 309 can be reserved for a different connected device. Additionally, in some implementations, the hub may reserve one or more allocation slots 309 for non-existent (dummy) devices to allow the hub device to sleep. In some implementations, each allocation slot 309 has a set size. In other implementations, the allocation slots 309 may have different sizes—for example, depending on the connection requirements.

An allocation slot 309 is begun by a polling request message 312 transmitted by the hub. BAN devices may sleep after receiving the allocation schedule message 311 until the start time of their scheduled allocation slot 309. Some desynchronization may occur during this sleep period. Accordingly, the BAN devices are programmed to wake up at least one guard time interval before their scheduled allocation slot 309. The guard time takes into account probable synchronization loss and is configured to cause the devices to wake a sufficient time before their allocation slot 309 to receive the polling request message 312.

Each polling request 312 can include a device address for the device allowed to transmit during the allocation slot 309. In some cases, the device address in the polling request 312 may not match the device scheduled to use the allocation slot 309 as indicated in the allocation schedule message 311. For example, this may occur if a BAN device's allocation slot 309 has been preempted for an emergency allocation slot.

A BAN device transmits to the hub after receiving a polling request message 312 addressed to the device. Accordingly, the device does not need to maintain an accurate network synchronization to become aligned with its allocation slot 309. Thus, in some embodiments the device can sleep between the allocation schedule message 311 and the allocation slot 309 without maintaining precise network synchronization and without requiring re-synchronization when waking.

The polling request message 312 may further include relative time offset, for example, the relative time offset information may comprise the current timeslot 318 position of the allocation slot 309. Other BAN devices, such as unconnected devices waking up to use the unreserved period 306 to build a connection, may use the time offset information contained in the polling request messages 312 to align to the network timing. This alignment may be used to reduce the time spent by unconnected device to search for the beacon 310. For example, if an unconnected device wakes up during after the reserved period 305, the unconnected device can listen to the next polling request message 312 to determine the current timeslot of the frame 301. The unconnected device can use this information to determine the time remaining in the current frame 301. The unconnected device may then reenter a sleep state for the remainder of the frame 301 and wake up in time to hear the next beacon 310. Accordingly, the polling request messages 312 provides power-saving to unconnected devices because they may be used by waking, unconnected devices to avoid having to remain awake until the next beacon 310.

The polling request message 312 may further include the duration of the allocation slot 309 (if the duration is not fixed during network operations), and the BAN device ID of the device able to use the allocation slot 309. If the allocation slot 309 has been preempted by an emergency request 307, the BAN device ID in the polling request message 312 can be configured to differ from the BAN device ID scheduled in the allocation schedule message 311.

After a SIFS 322, the device identified in the polling request message 312 (the polled device) transmits an uplink response 313, comprising an uplink data packet or a polling response message indicating no uplink data. After the response 313, the hub transmits a downlink response 314. The downlink response 314 comprises an acknowledgement (ACK) of the uplink data packet (if transmitted) and a downlink data packet (if the hub has downlink data). In some implementations, each allocation slot 309 may have more than one packet exchange 313, 314. Subsequent uplink packets 313 include an ACK for the previous downlink data packet 314.

There is no set division between uplink traffic 313 and downlink traffic 314 during an allocation slot 309. This reduces complexity and allows devices to sleep more often. Rather the allocations schedule message 311 simply schedules the start time (and, in some cases, length) of the allocation slot 309.

The polled device may reenter a sleep state after the last downlink response 314. If the messages 313 and 314 do not take up the entire allocation slot 309, the hub may also sleep for the remainder of the allocation slot 309. Additionally, if the polled device does not transmit a response 313, the hub can use the allocation slot 309 to sleep.

The reserved period 305 ends after the last scheduled allocation slot 309. Accordingly, the length of the reserved period 305 can be configured to vary between consecutive frames 301. Additionally, in some embodiments, the reserved period 305 may not occur in a frame 301 if no allocation slot 309 is scheduled for the frame 301.

An unreserved period 306 occurs after the reserved period 305 (or after the emergency period 303, if there is no reserved period 305). In some embodiments, the reserved period 305 has a maximum length to ensure that there is a predetermined minimum length for the unreserved period 306.

BAN devices use the unreserved period 306 to build a connection with the hub or to transmit bursty uplink data to the hub. Additionally, new network devices begin (or conduct) the association process 202 (FIG. 2) during the unreserved period 306. Devices may also use the unreserved period 306 to rebuild lost connections or change connection parameters. Furthermore, emergency-capable devices may use the unreserved period 306 in the same manner as the emergency period 303.

The BAN devices can be configured to use a contention-based access mode to access the channel during the unreserved period 306. For example, the contention-based access mode may be slotted ALOHA, CSMA/CA, p-persistent ALOHA, or p-persistent CSMA. The contention based-access mode during the unreserved period 306 may be the same or different than the one used during the emergency period 303 (if one is used during the emergency period 303).

The unreserved period 306 in this example begins with a polling broadcast message 315 broadcast by the hub. In some implementations, a broadcasting destination address (broadcasting ID) is established. The polling broadcast message 315 (and other broadcast messages 310, 311) may use the broadcasting ID.

Devices that woke in time to receive the beacon 310 and allocation schedule message 311, will know the start time of the unreserved period 306 form the allocation schedule message 311. They may then sleep a short time during the reserved period 305 and wake up in time to receive the polling broadcast message 315. Like the scheduled devices, the unconnected devices waking for the unreserved period 306 may wake a predetermined guard interval before the polling broadcast message 315. While they may lose some network synchronization during the short sleep, they can rely on the end of polling broadcast message 315 to begin transmitting.

The polling broadcast message 315 may also include timing information (such as the starting timeslot of the unreserved period 306) to allow devices waking from an unconnected state to synchronize to the network.

Devices can be configured to transmit uplink management messages 316 to the hub. These uplink management messages 316 may comprise connection request messages, emergency connection request messages, emergency reporting messages, uplink data packets, association requests, and other management messages. In response, to a received uplink message 316, the hub responds with an appropriate management response 317, such as a connection request response, an emergency connection response, an ACK of an uplink data packet, an association response, or responses to other management messages.

An emergency request message sent during the unreserved period 306 may be similar to an emergency request message 307 sent during an emergency period 303. In some implementations, during the unreserved period 306, emergency request messages are given a higher priority than other messages 316. For example, a shorter inter-frame spacing 322 or smaller contention window size may be used for emergency request messages.

Figure 4:
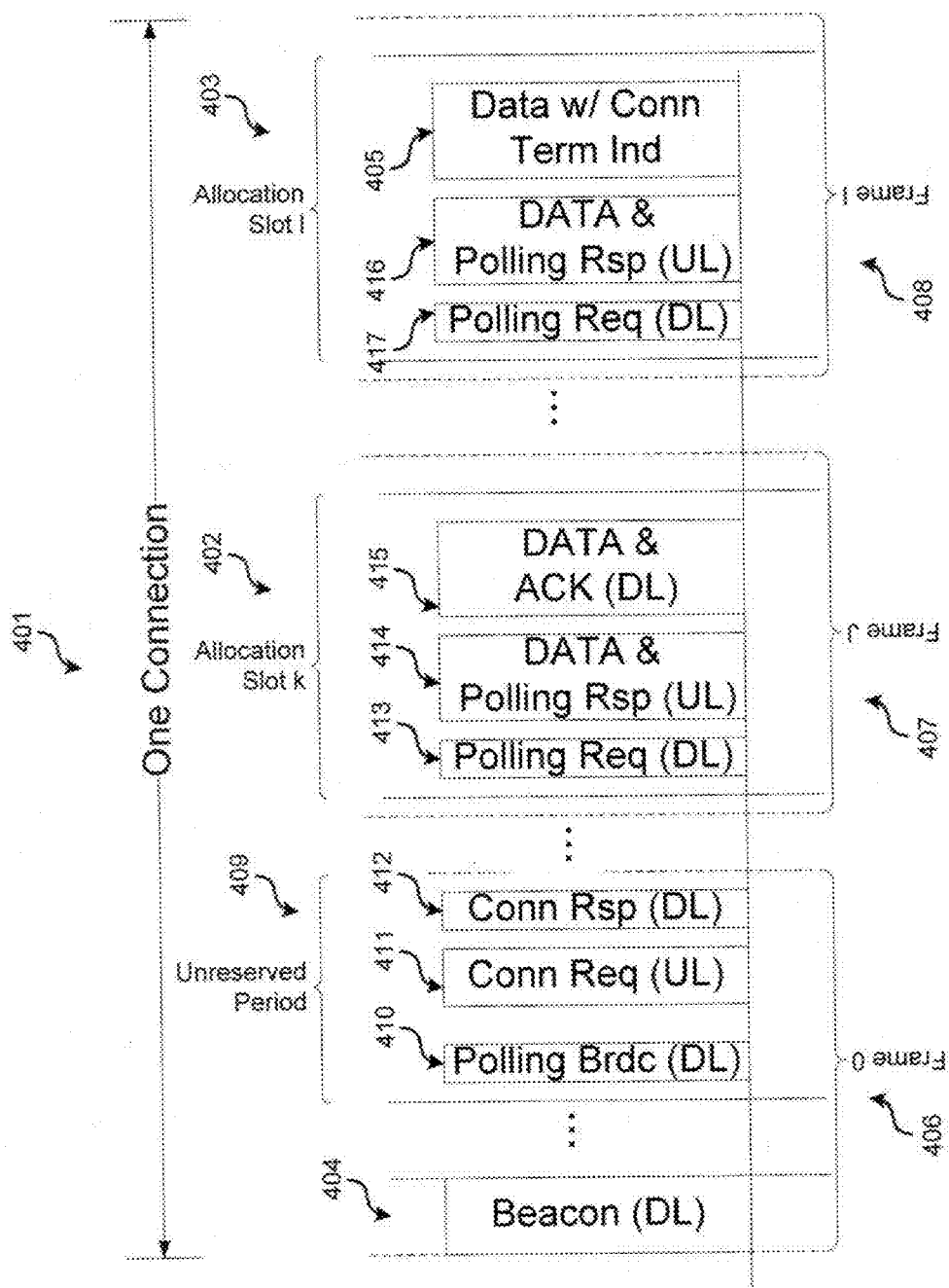
FIG. 4 illustrates an example connection for a BAN device during BAN operations.

FIG. 4 illustrates the life span of a connection 401 between a hub and a connected device in accordance with one embodiment of the technology described herein. The connection in this example comprises a first frame 406 where the connection is built and subsequent frames 407, 408 where communication takes place during corresponding allocation slots 402, 403. In some implementations, the number of frames between connection frames 407, 408 may vary depending on connection. For example, a connection, such as an emergency connection for a monitoring device, may have an allocation slot 402, 403, scheduled every frame. Another connection may have allocation slots 402, 403 scheduled every other, every third, or every nth frame.

The example connection 401 begins during the unreserved period 409 of a first frame 406. The device building the connection uses the beacon period 404 (or a polling message 312, 315 (FIG. 3) to synchronize to the network timing. During the unreserved period 409 of frame 406, the device listens to the polling broadcast 410 and exchanges a connection request 411 and response 412 with the hub. For non-emergency connections, the connection request 411 and response 412 are used to set the connection parameters for the connection 401. Connection parameters may include the duration of the connection 401, number of frames between allocation slots 402, 403, the data rate used during the connection, priority, traffic direction, allocation slot 402, 403, durations, whether encryption will be used, and other connection parameters. For emergency connections, the connection parameters are set during the association process and the connection request 411 and connection response 412 are used to set up a connection 401 according to these predetermined connection parameters.

During the subsequent frames 407, 408 of the connection 401 (typically the frame immediately after the first frame 406), the device may have allocation slots 402, 403 scheduled for it. As discussed above, the allocation slots 402, 403, can include polling requests 413, 417; uplink data or polling response messages 414, 416; and ACK or downlink messages 415, 405.

Additionally, the last downlink message 405 may include a connection termination indication. In some implementations, the connection 401 length is extended in certain circumstances. For example, the connection 401 may be extended if unexpected uplink or downlink traffic is generated during the connection, or if one or more allocation slots 402, 403 are preempted by an emergency connection. In these implementations, the device will continue listening to schedules (at the frame frequency between allocation slots 402, 403) until the downlink message 405 with connection termination indicated.

Figure 5:
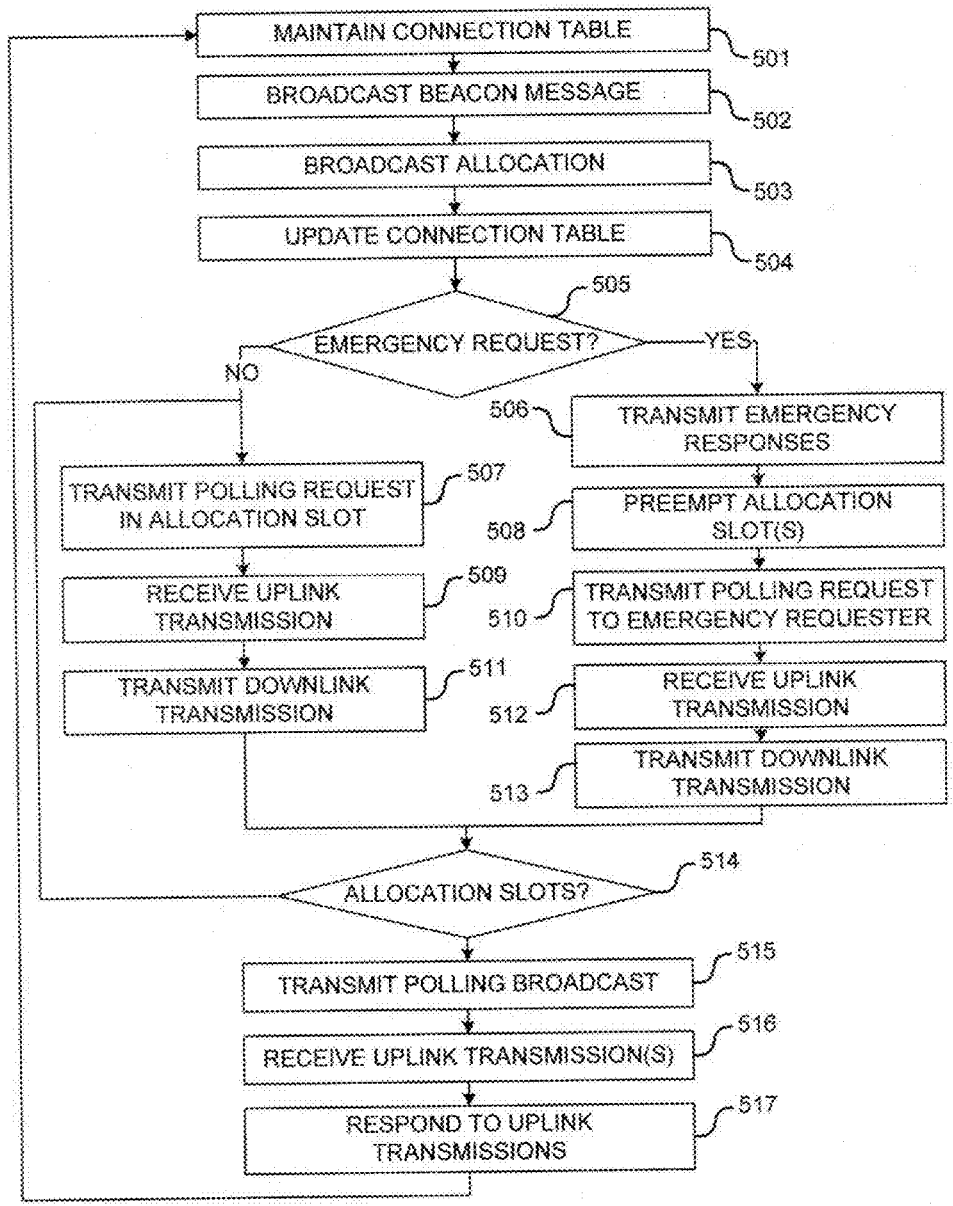
FIG. 5 illustrates an example of hub operations during BAN operation.

FIG. 5 illustrates a method of network operation in accordance with one embodiment of the technology described herein. The hub maintains a connection table 501 to schedule allocation slots for BAN devices. For each new connection, the step 501 comprises the hub adding an entry to the connection table. An example connection table is presented in FIG. 6. Each entry of the example connection table includes: (a) a connection ID; (b) the connection duration as a number of frames; (c) the connection priority; (d) the negotiated allocation slot length as a number of timeslots; (e) the number of frames between allocation slots; (f) an in-allocation flag field; (g) a holding time as a number of frames; (h) the number of frames since the last allocation slot; and (i) an allocation adjustment as a number of timeslots. Certain entries of the allocation table may be set during the connection process (for emergency connections, during the association process), such as the connection ID, connection duration, connection priority, negotiated allocation slot length, and number of frames between allocation slots. Additionally, in certain implementations, emergency connections are assigned a highest connection priority unavailable to non-emergency connections.

After a frame ends, during step 501, the hub sorts the connection table by priority. Connections with higher priorities are given allocations 309 (FIG. 3) preferentially. After sorting, the hub uses the allocation gap and last allocation information to determine if a connection needs an allocation in the coming frame. The hub updates the in-allocation flag to 1 if a connection needs an allocation in the coming frame.

Next, as part of step 501, the hub fulfills the allocation for the connections with in-allocation flag equal 1. The allocation information can be stored in the hub in a format similar to the allocation schedule message 311 (FIG. 3). If the total allocation slots needed to fulfill the needed connections exceeds the available time of the reserved period 305, then allocations for connections with lower priorities are not fulfilled. The unfulfilled allocation lengths are added to the unfulfilled connection's allocation adjustment field. If the total allocation does not exceed the length of the available reserved period 305 (FIG. 3) length, then the hub may allocate an empty allocation slot before the unreserved period 306 to save power.

In step 502, the hub starts the current frame by broadcasting the beacon message 310 (FIG. 3). In step 503, the hub broadcasts the allocation schedule determined during step 501. After transmitting the beacon 502 or the allocation schedule 503, the hub updates the connection table 504 by adding one frame to the holding time and last allocation fields for all entries.

Next, the hub listens during the emergency period to determine if there are any emergency requests 505. If the hub hears an emergency request, the hub transmits an emergency response 506 and builds an emergency connection (which may include updating the connection table).

As part the first frame of the emergency connection, the hub preempts 508 one or more of the first allocation slots of the reserved period to build an emergency allocation slot. FIGS. 7A and 7B illustrate an example of preemption 508. Referring now to FIGS. 7A and 7B, at the beginning 701 of the current frame's reserved period, a plurality of allocation slots 702, 703, 704, 705, 706 are scheduled. In this example, during the association process, the emergency connection had a negotiated allocation length greater than the length of allocation 702. Accordingly, both allocation slots 702 and 703 are preempted and an emergency allocation slot 707 is provided for the emergency-requesting device. Allocation slots 708, 709, 710 proceed as scheduled. During step 508, if a connection has its allocation slot preempted, the length of the preempted allocation is added to the preempted device's allocation adjustment entry.

Returning to FIG. 5, in step 510, the hub begins the emergency allocation slot 707 by transmitting a polling request to the emergency requester. The polling request transmitted in step 510 can include the device ID of the emergency requester, not the device that was originally scheduled slot 702. The hub may then receive uplink emergency transmissions 512 from the emergency requester and provides any required downlink traffic 513, including ACKs.

If an emergency request is not received 505, then the hub transmits a polling request 507 to the first scheduled device to begin the first scheduled allocation slot. The allocation slot proceeds with the hub receiving uplink traffic 509 and transmitting downlink traffic 511 to the scheduled device.

In both cases 505, at the end of each allocation slot, the hub clears the in-allocation flag and updates the last allocation field, and if necessary, the adjustment field. If the hub uses the current allocation slot for extra management messages, it also adds compensation to the adjustment field. During subsequent scheduling 501, the adjustment allocation decreases only after the holding time reaches the connection duration. When the adjustment allocation reaches 0, the hub terminates the connection.

After the scheduled (or emergency) allocation slot, the hub repeats 514 for the remaining scheduled allocation slot(s) (and the remaining emergency allocation slot(s), if multiple emergency requests were received).

After the reserved period, the hub begins the unreserved period by transmitting the polling broadcast message 515. Then, during the unreserved period, the hub receives 516 and responds 517 to any uplink transmissions.

As discussed herein, nodes can be configured to transmit or receive packets from multiple traffic sources. Examples of these sources can include high QoS UL traffic, low QoS DL traffic, and so on. Accordingly, in various embodiments, the reservations can be configured such that a given reservation can accommodate multiple traffic sources to allow shorter awake times and lower power consumption.

Various embodiments can also be implemented in which signaling traffic may be included in reserved allocation slots. Accordingly, in some embodiments an in-band signaling technique can be used to insert signaling traffic into data flows.

However, inserting additional traffic sources into pre-existing reservations can result in a change in the original reservation schedule. Accordingly, where constant traffic is inserted (e.g., DL traffic becoming DL/UL traffic) the signaling process can be used to update the schedule. In some embodiments, the hub is configured to make an appropriate scheduling adjustment to allow the existing reservation adapt to the traffic fluctuations. This is described in greater detail below.

With conventional reservation-based MAC, the boundaries between the nodes' reservations are fixed. This limits the flexibility of packet transmissions. In various embodiments, updated reservations may be allowed to extend beyond the original reservation boundary to accommodate additional traffic. In some embodiments, a preemption mechanism may be employed to allow nodes to cross the reservation boundaries and preempt one or more nodes in subsequent reservation slots.

Figure 8:
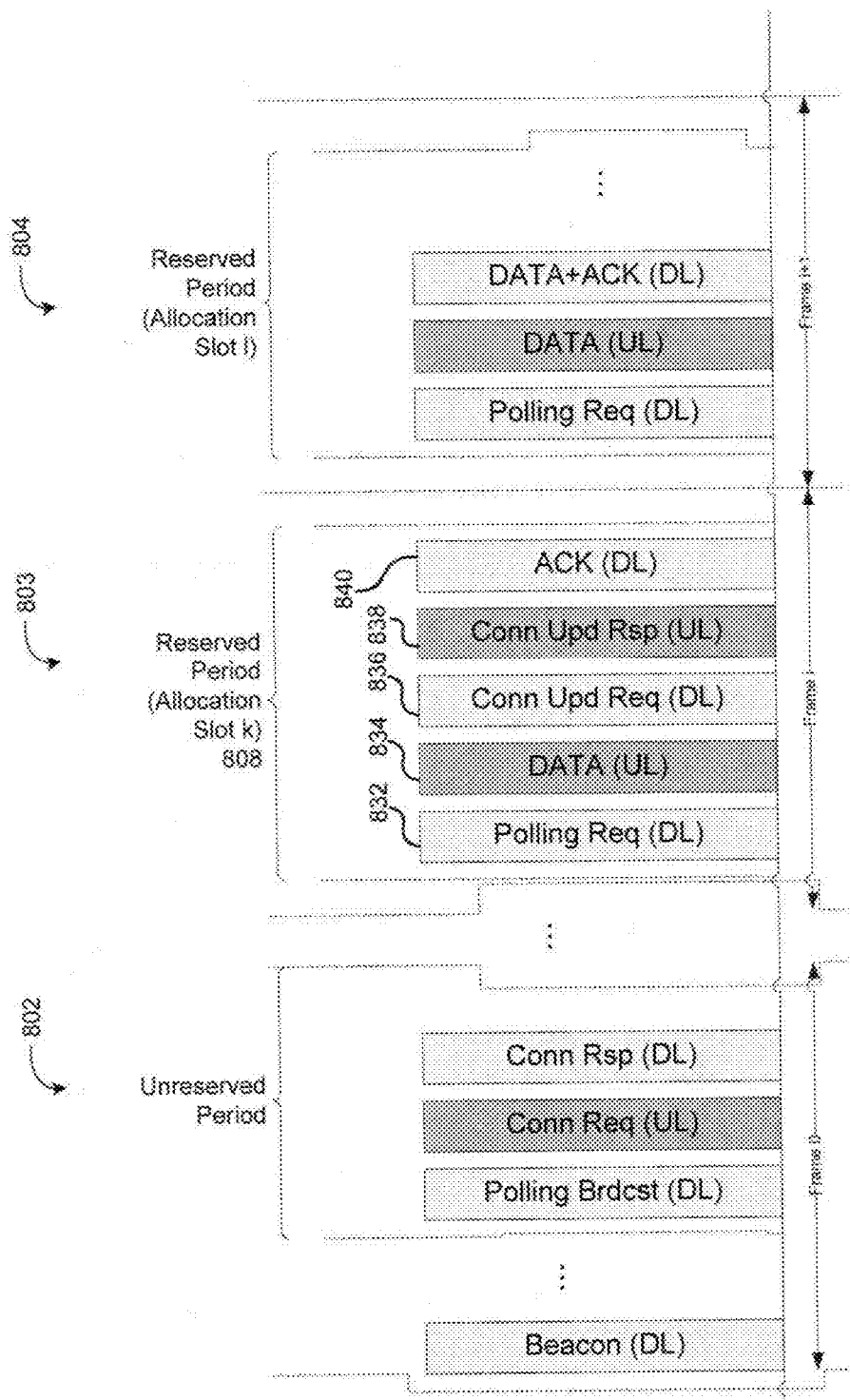
FIG. 8 is a diagram illustrating an example of in-band signaling.
Figure 9:
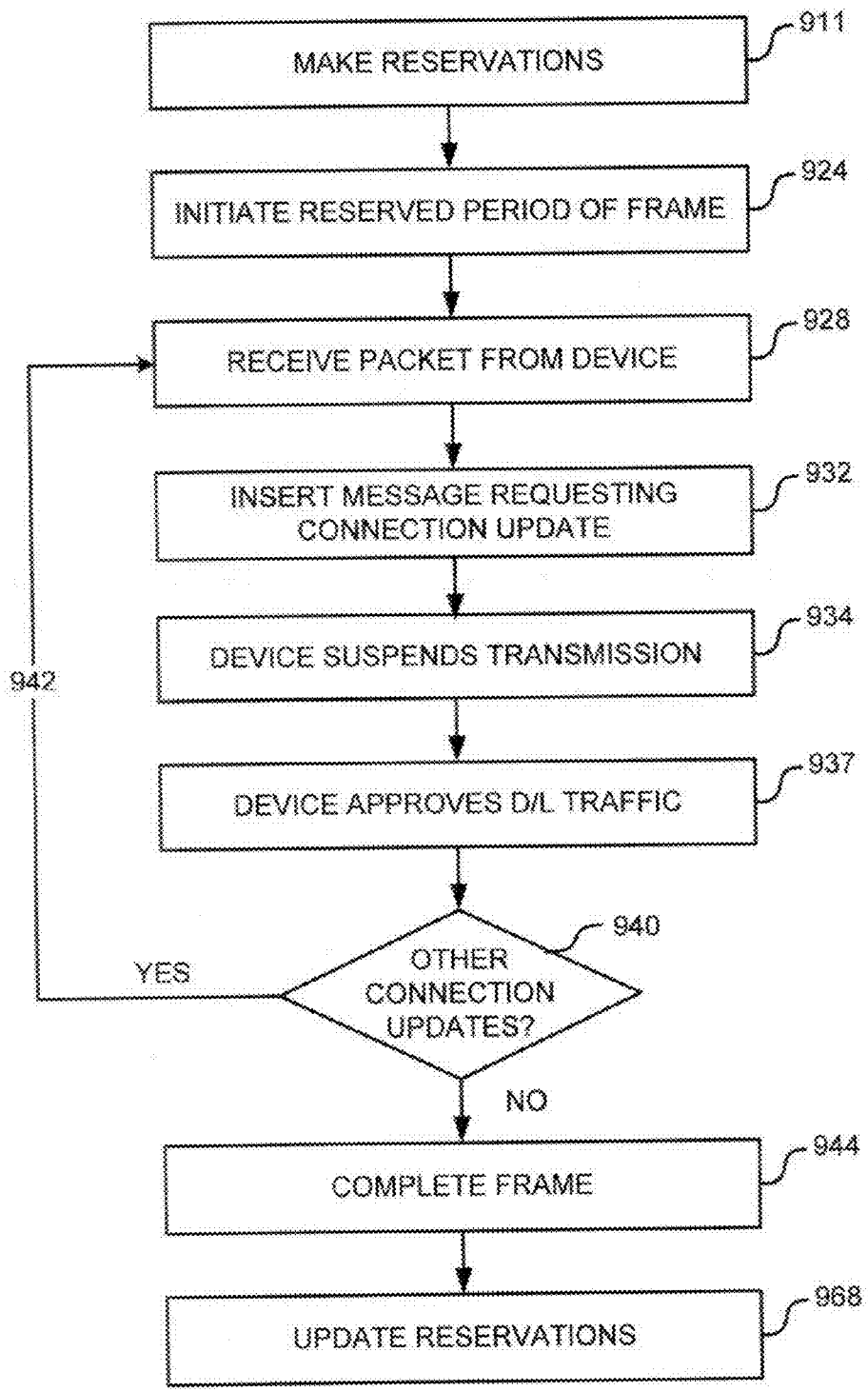
FIG. 9 is an operational flow diagram illustrating an example process of in-band signaling in accordance with the scenario illustrated in FIG. 8.

FIG. 8 is a diagram illustrating one example of in-band signaling in accordance with one embodiment of the technology described herein. FIG. 9 is an operational flow diagram illustrating an example process of in-band signaling in accordance with the scenario illustrated in FIG. 8. The example illustrated in FIGS. 8 and 9 contemplates a scenario in which the hub seeks to add additional traffic to a preexisting reservation. More particularly, in this example, the hub seeks to add downlink traffic to an existing reservation for uplink traffic in Frame i 803 (FIG. 8). Referring now to FIGS. 8 and 9 at operation 911 the network devices and the hub make the reservations for a given frame 803. Although not illustrated in FIG. 8, frame 803 can include one or more of a beacon period, a schedule period, an emergency period, a reserved period and an unreserved period. At 924, the reserved period 808 of frame 803 is initiated. As shown in this example, at or near the beginning of reserved period 808, the hub initiates a polling request 832. In response, a network device uplinks data to the hub as illustrated at 834. At 928, the hub receives an uplink data packet 834 from the device.

At operation 932, the hub inserts a Connection Update Request message 836 after it correctly receives a data packet. In one embodiment, the update request message 836 is sent during the uplink data transmission. At operation 934, the device suspends its data transmission and answers the hub. In this example, the response is a Connection Update Response message 838, approving the downlink traffic. The approval is shown at operation 937. There can be circumstances in which the device does not approve the additional downlink traffic such as, for example, when the channel limit has been reached. An in-band signaling mechanism configured in this way can be used to combine all traffic related to one corresponding node to one allocation slot or to a consecutive group of allocation slots. In such configurations, the sensors only need to wake up for the single consecutive period and can remain or go back to sleep for the rest of the frame.

At operation 940, if there are other connection updates to be made, the hub communicates with the corresponding device as illustrated by flow line 942. Otherwise, the frame completes at operation 944. After the current frame 803, the hub uses the new connection parameters and assigns the new reservations for the new UL/DL traffic of the corresponding body sensor(s) for the next frame 804. This is illustrated at operation 968. When a connection has been updated through the in-band signaling process, the hub updates its connection parameters, including the priority, in the connection table (e.g., FIG. 6) and makes new reservations for this connection for the next frame.

Figure 10:
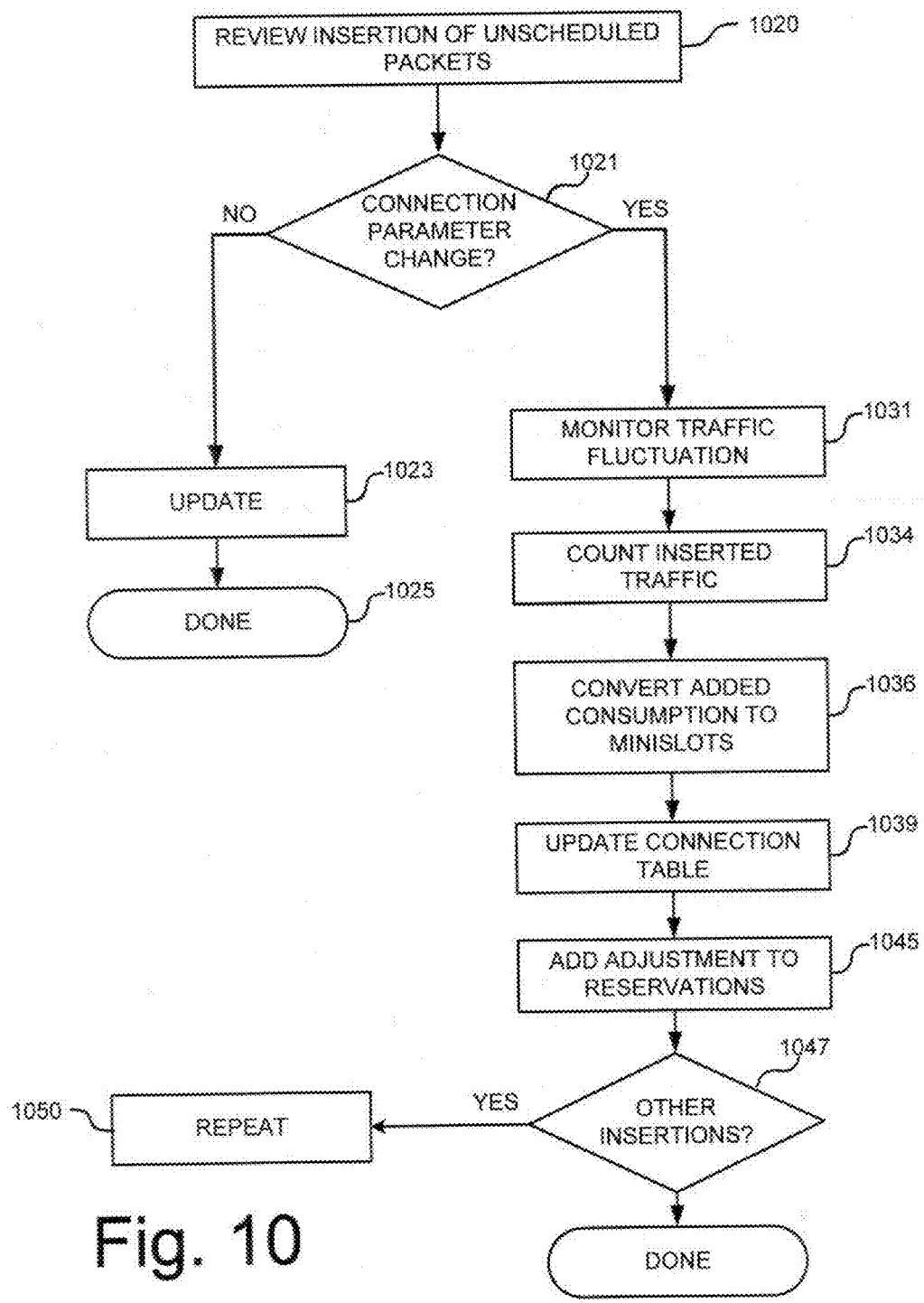
FIG. 10 is a diagram illustrating an example for updating or assigning new reservations.

FIG. 10 is a diagram illustrating an example for updating or assigning new reservations in accordance with one embodiment of the technology described herein. At operation 1020, the hub reviews the insertion of unscheduled packets. If the insertion of unscheduled packets does not result in a change to the connection parameters, there is generally no need to update the connection table and make new reservations. However, in some embodiments the hub may still adjust the next frame's reservation according to the volume of traffic inserted in the current frame. The Allocation Adjustment field in the connection table may be used for this purpose. This is illustrated at 1021, 1023 and 1025. This process can be repeated for each node for which traffic was added as illustrated by operations 1047 and 1050.

In various embodiments, the hub can be configured to monitor the instant traffic fluctuation of each body sensor or device and count or otherwise determine the amount of inserted traffic. This is illustrated by operations 1031 and 1034. At operation 1036, the count can be converted to a quantified number of mini slots, and that value used to update the Allocation Adjustment field in the connection table. This is shown at operation 1039. During the scheduling process, the hub adds the Allocation Adjustment value to the corresponding reservations as shown at operation 1045. If the total allocation adjustment cannot be fulfilled due to channel limit, the one with higher priority should be fulfilled earlier. The allocation adjustment can be done without extra signaling between the hub and the devices because the hub is aware of the traffic fluctuation of each device.

To avoid disrupting ongoing transmissions, the inserted signaling messages in some embodiments continue the acknowledged sequence number as if the transmission/acknowledgement is continuing. Due to the bi-directional property of the signaling message exchange, these in-band signaling messages can be configured to carry their own sequence number as well. Although acknowledge, or ACK, messages are not in-band signaling, they can in some embodiments be configured to acknowledge the sequence number of last in-band signaling message, i.e. Connection Update Response in the example of FIG. 8. In cases where the traffic changes from single-directional to bi-directional, in some embodiments both the sequence number and the acknowledged sequence number can be made to appear in the MAC header. In addition, to avoid state machine errors in this type signaling exchange, special message types or other methods can be used to trigger the transitions of the FSM (finite state machine).

In various applications, in-band signaling can be configured to allow signaling in an Unreserved Period (e.g., period 802) as well. Accordingly, in some embodiments, the devices can be configured to send out the request in Unreserved Period If the scheduled reservation of a node is not enough for the unscheduled signaling exchange. Additionally, other unscheduled traffic can be inserted into a current reservation, no matter what the direction of current traffic is. To minimize or avoid the potential processing errors caused by the inserted packets, the inserted packets can be configured to carry the sequence number field with continuing values and the acknowledged sequence number acting as the ACK message to the last received data packet.

In various implementations, one reserved allocation slot can be configured to contain transmissions for several packets. Accordingly, the reservation ideally takes into account changes to the wireless channel's condition so that in at least in many or most cases, the reserved allocation slots are sufficient to accommodate the scheduled packets. However, there may be cases where the desired traffic volume exceeds the reservation. For some types of traffic, packets can be dropped where the volume exceeds the reservation with little or no impact to device performance. However, other types of traffic cannot be dropped. In instances where it is preferred not to drop traffic, the system can be configured to extend the current reservation (such extensions are described below with reference to Sensor-initiated Grant Extensions). Such extension may result in delay or even preemption of one or more subsequent reservations in the reserved period.

However, such delay or preemption can result in the unnecessary consumption of power by the delayed or preempted device. Because devices are scheduled to wake up based on the existing reservations, a device that wakes up at its scheduled time, but whose reservation has been delayed due to insertion of traffic in prior allocation slots, remains awake to wait for its delayed communication. Accordingly, its awake time is longer than would otherwise have been the case.

In some embodiments, the affected body sensors can regain the assigned allocation slots with a certain allowed delay. Accordingly, the extension of the reservations becomes feasible. However, even when the extension does not exceed the channel limit, the delay and the extra awakening time are not desirable for the body sensors. A delay within one frame usually will not deteriorate the QoS substantially. But a delay crossing frame boundaries can undermine the QoS greatly. Additionally, as noted above, the longer awake time runs counter to the objective of saving power in BANs. Accordingly, various embodiments can be implemented to reduce the impact of the delay.

In one embodiment, a gap can be added between two adjacent allocation slots. Accordingly, a given allocation slot would not begin as soon as the prior allocation slot ended. Instead, a small delay, or gap, is inserted between the adjacent allocation slots. Therefore, when traffic is added to a given reservation, the traffic can be allowed to extend into the gap without impacting the next reservation. However, in cases where reservations are not extended and one or more gaps remain unused, these unused gaps consume bandwidth that could otherwise be schedulable. With BAN systems, however, this may not be an issue as the throughput or the bandwidth efficiency is typically not the primary concern of BAN systems. In some embodiments, gaps can be added after each allocation slots, while in other embodiments, gaps are only added after some allocation slots (e.g., allocation slots designated for devices handling priority traffic).

In a further embodiment, devices can be configured to allow a maximum extra awakening time for body sensors in the event the scheduled Polling Req messages do not arrive at the scheduled time. Accordingly, the hub or devices can specify a maximum awake time for circumstances in which a device awakens for a scheduled communication and the communication does not arrive in time.

Figure 11:
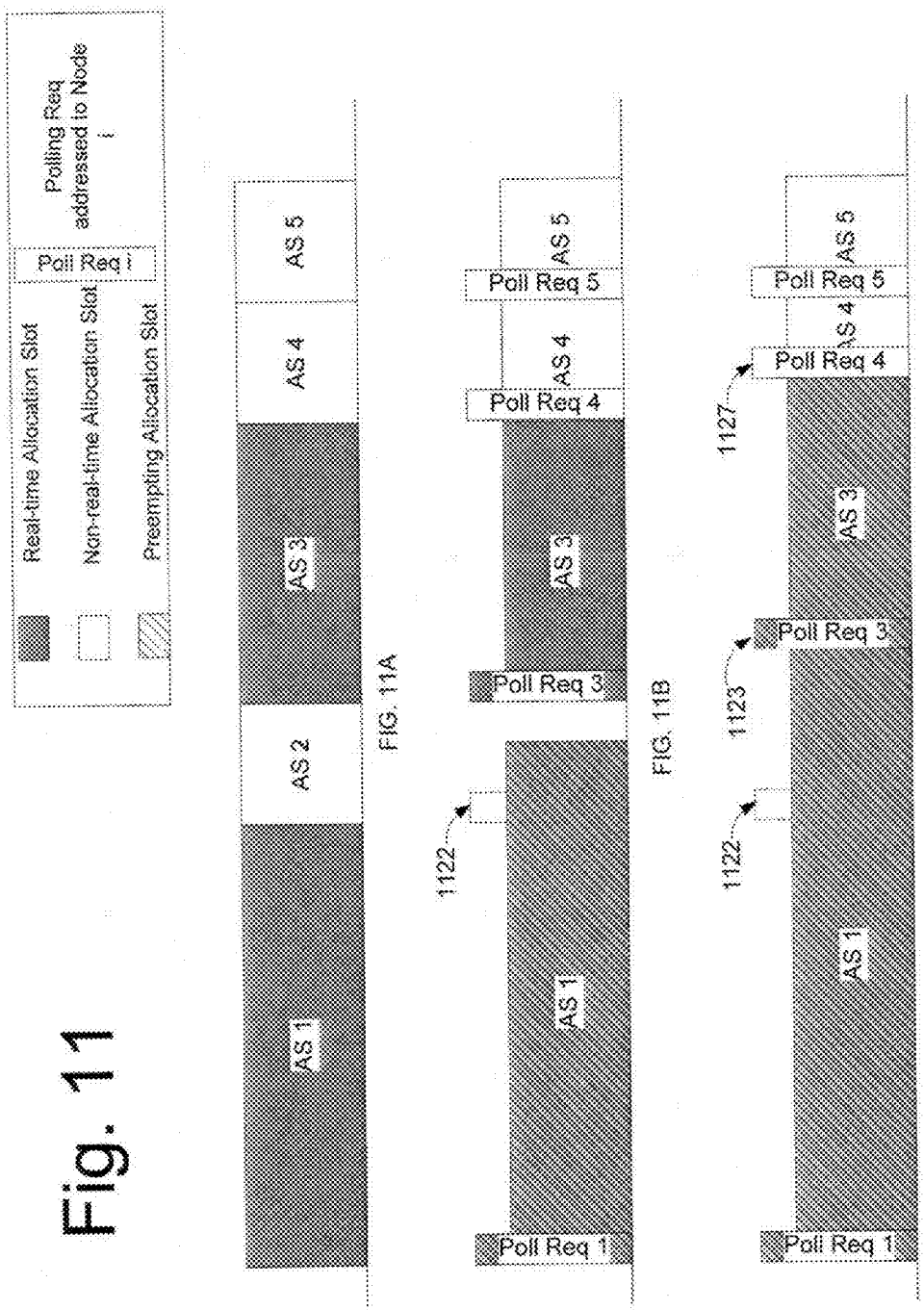
FIG. 11, which comprises

A preemption mechanism can also be used so that allocation slots can be extended to their adjacent slots. In some embodiments, a preferential mechanism can be implemented such that some allocation slots are permitted to be extended while others are not allowed to be extended. In some embodiments, the case of preemeption by emergency is a special case of this example preemption mechanism. FIG. 11, which comprises FIGS. 11A, 11B, and 11C, is a diagram illustrating an example preemption mechanism in accordance with one embodiment of the technology described herein. In this example, it is assumed that there is an existing priority rule that defines the preemption conditions and settles the optimum arrangement for different allocation slots having different priorities.

In the example shown in FIG. 11A, the original schedule of allocation slots includes reservations for five nodes, shown by allocation slots AS1-AS5. Further in this example, Node 1 and Node 3 have reservations of real-time traffic as depicted by the shading of their respective allocation slots AS1, AS3. To illustrate examples of preemption, it is assumed for this discussion that after the original schedule is made, traffic is added to the Node 1 communication. FIGS. 11B and 11C depict two possible fulfillments of this modified schedule, both of which have a form of preemption taking place. In FIG. 11B, Node 1 extends its allocation slot and preempts part of the allocation slot AS2 of Node 2. As illustrated, Node 2 misses its Polling Req because the window 1122 for that request was preempted by Node 1. Accordingly, Node 2 cannot fulfill its reservation. However, because the Node 1 communication does not extend past the end of AS2, the remainder of the nodes (i.e., Nodes 3, 4 & 5) follow the original schedule.

In FIG. 11C, due to the amount of added traffic, Node 1 preempts not only the whole allocation slot of Node 2 but also part of the allocation slot of Node 3. As with the example in FIG. 11B, here Node 2 cannot fulfill its reservation because the window 1122 for its Poll Req was preempted by Node 1. However, because Node 3 handles high priority, real-time traffic, Node 3 receives a delayed Polling Req 1123. Because Node 3's real-time traffic is a higher priority than that of Node 4, Node 3 preempts part of Node 4's allocation slot. Node 4 also receives a delayed polling request and fulfills the remainder of its allocation slot, but does not preempt Node 5's allocation slot.

In various embodiments, the nodes whose allocation slots have been preempted can still have the chance to fulfill their allocation slot in the same frame, either partially or fully. For example, if the preempting allocation slot can end within a certain range after the scheduled starting point of the preempted allocation slot, the hub can send out the delayed Polling Req and the preempted nodes can start their allocation slot with a certain amount of delay. If in this case the preempted node can further preempt another node's allocation slot, it can fulfill the allocation slot fully. This example is shown in FIG. 11C in which Node 3 preempts part of Node 4's slot to complete its communication. Alternatively, a node may use only the remaining portion of its allocation slot, and not further preempt other nodes. This example is shown by Node 4 in FIG. 11C. Accordingly, as these examples illustrate, preemption can be governed by the relative priorities of the Nodes, or it can be used on an emergency basis. Ideally, in some embodiments, the hub is configured to inform the preempting nodes know how long the preemption can last. Additionally, the hub can be configured to limit or control the frequency with which a given node preempts other nodes, or to control preemption generally, to avoid or limit preemption happening repeatedly. For example, the hub can be configured to dynamically adjust the gap to help reduce the amount of preemption that is occurring.

Figure 12:
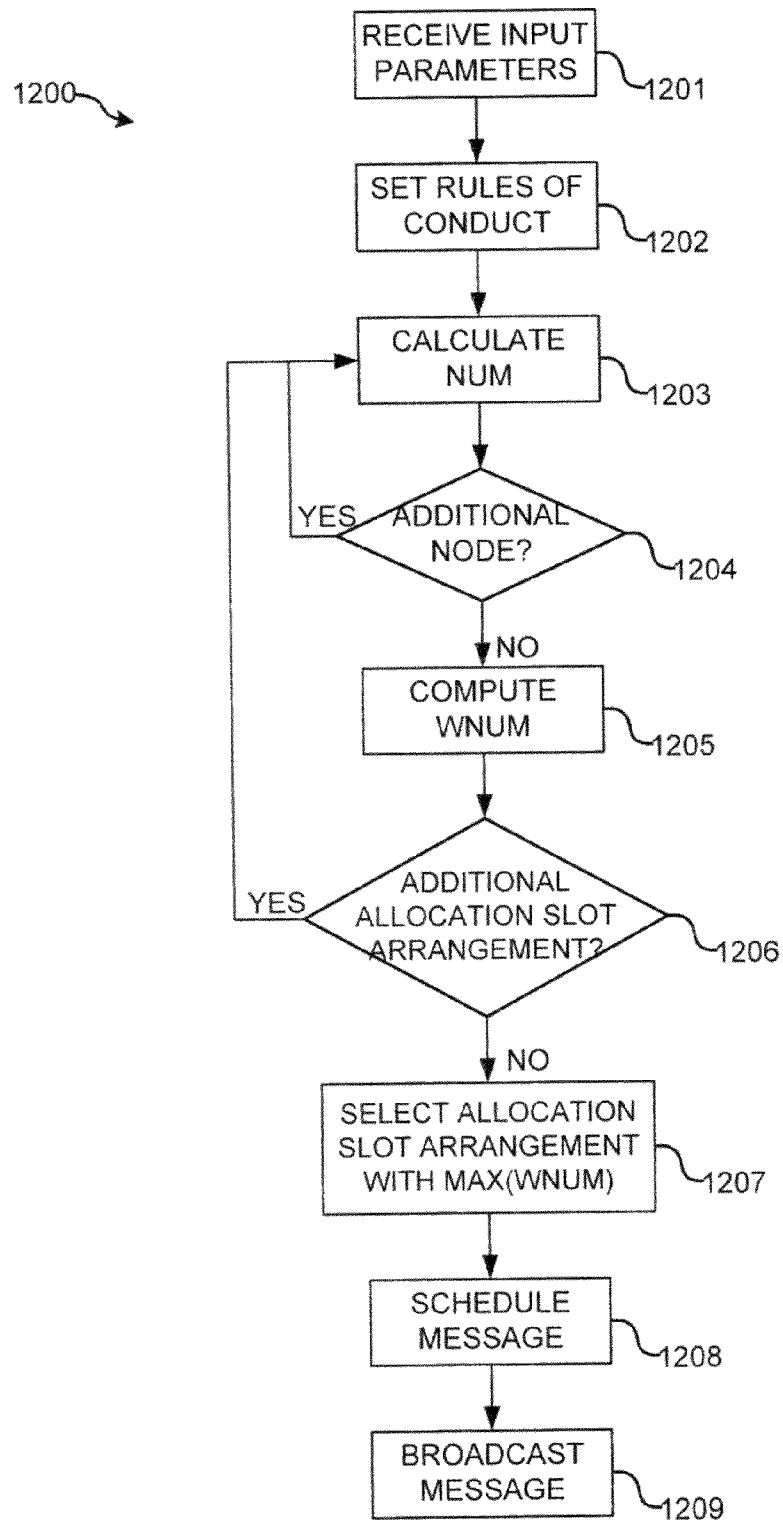
FIG. 12 is an operational flow diagram illustrating an example process of arranging allocation slots.
Figure 13:
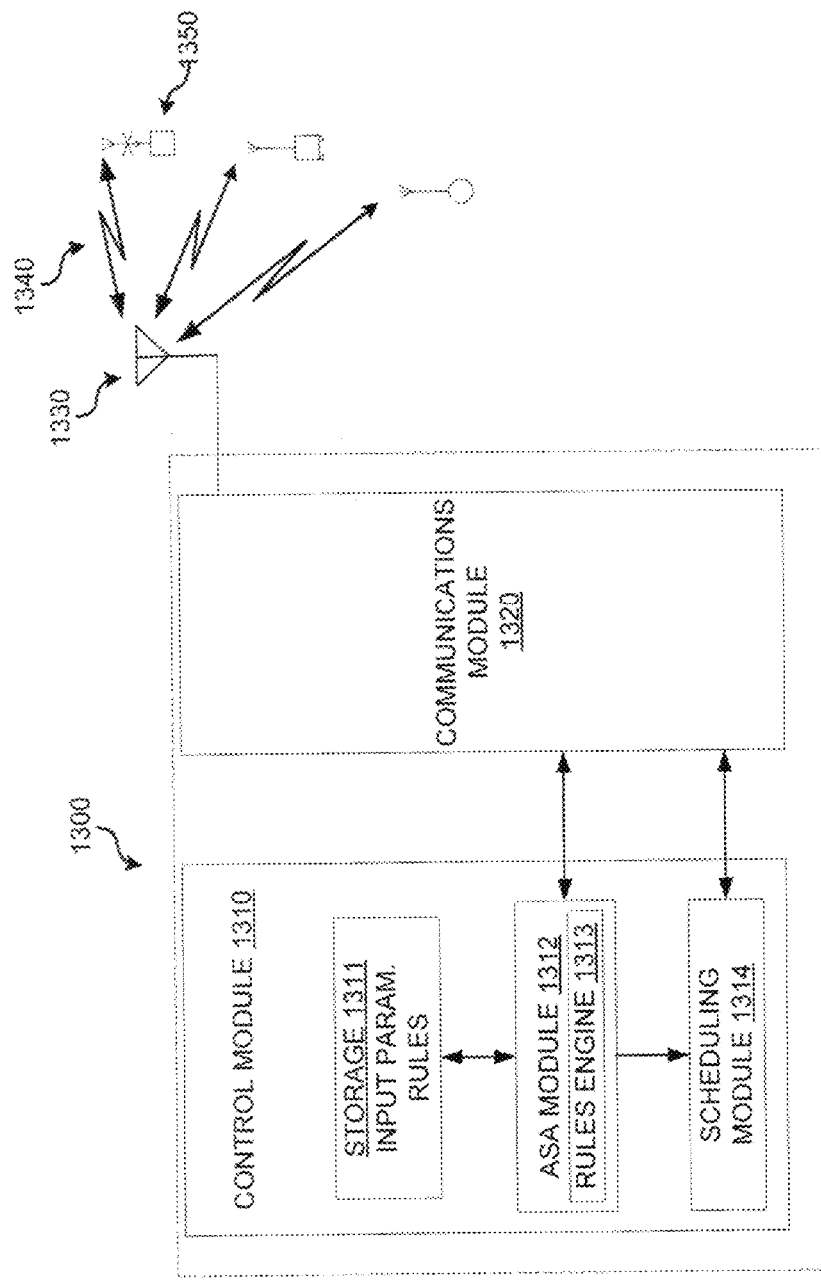
FIG. 13 is a functional diagram illustrating a BAN hub that can perform the process of FIG. 12.

FIG. 12 is an operational flow diagram illustrating an exemplary allocation slot arrangement process 1200 in accordance with one embodiment of the systems and methods described herein. FIG. 13 is a functional diagram illustrating an example of a BAN hub 1300 that can perform the process of FIG. 12. BAN hub 1300 may comprise a control module 1310, communications module 1320, and transceiver 1330. Control module 1310 may comprise storage 1311, an allocation slot arrangement ("ASA") module 1312 and a schedule module 1314. ASA module 1312 may comprise an application configured to performed allocation slot arrangement. In some embodiments, ASA module 1312 and schedule module 1314 may be integrated as a single module. In other embodiments, ASA module 1312 may comprise additional modules configured to perform other operations in addition to allocation slot arrangement and scheduling. Communications module 1320 may be configured to cause transceiver 1330 to broadcast arranged allocation slot scheduling information to nodes 1350 via downlink connection 1340. Each node 1350 may comprise a BAN device such as a medical body sensor unit (e.g. EEG, glucose, blood pressure, or ECG) or entertainment unit (e.g. sports or video games). In other embodiments, a BAN device may comprise a plurality of nodes.

At operation 1201, BAN hub 1300 receives a set of input parameters that may be used for calculating an allocation slot arrangement. These input parameters may correspond to the maximum length of the reserved period, emergency event parameters, and characteristics of the nodes 1350 in the BAN. Input parameters may be stored on storage 1311 in BAN hub 1300. Some or all of these input parameters may be retrieved from a connection table that BAN hub 1300 uses to schedule allocation slots for BAN devices. Other input parameters (e.g. emergency event parameters, Sensor-initiated Grant Extension parameters, node weight factors, reschedule tolerance threshold) may be predefined and stored in storage 1311. A creator of an application configured to perform allocation slot arrangement may predefine the input parameters. In other embodiments, the user of the BAN network may predefine the input parameters.

FIG. 14 illustrates an exemplary table of input parameters that may be received by BAN hub 1300 at operation 1201. In this example, the maximum length of the reserved period is L. Emergency event parameters may be included and may comprise the probability ($p_0$) and length distribution $f_{x_0}(x_0) \sim \exp(\lambda_0)$ of emergency events. Parameters for a node n may also be included and may comprise a weight factor ($w_n$), the scheduled allocation slot length ($l_n$), a reschedule tolerance threshold ($R_n$), and a SiGE probability ($p_n$) and length distribution ($f_{x_n}(x_n) \sim \exp(\lambda_n)$). Although this set of parameters is used for developing a mathematical formulation for allocation slot arrangement (described below), in other embodiments additional or alternative parameters may be used.

A reschedule tolerance threshold $R_n$ indicates how many mini slots a corresponding node will wait before going back to sleep if the Polling Request does not arrive in time.

A node weight factor $w_n$ depends on the node's QOS requirements in terms of latency and reliability. For example, ECG and entertainment audio are both real-time periodic data and their late arrival may hinder performance or render them useless. However, physiological data monitoring usually is more important than entertainment. Accordingly, nodes with ECG data traffic would generally be assigned a higher weight factor. The assignment of weight factors may be context dependent. Weight factors for medical sensor node traffic (e.g. ECG, EEG, EMG, pH-level monitor, respiration monitor, blood pressure measurement, and glucose monitor) may vary depending on a patient's conditions. If a node monitors glucose levels of a diabetic patient, for example, it may be assigned a high weight factor. In other embodiments, the weight factors assigned for given nodes may be invariable.

A Sensor-initiated Grant Extension ("SiGE") is an extension of an allocation slot duration beyond the granted allocation slot duration. These extensions may occur dynamically. For example, a SiGE occurs when multiple PHY layer packet drops require a node to extend its allocation slot duration to allow for retransmission of the packet. A SiGE also occurs when an allocation slot is used for in-band signaling (as opposed to data transfer) to insert signaling traffic into data flows. In further embodiments, a SiGE occurs when a node extends its allocated slot to avoid falling behind its QOS requirements.

At operation 1202, a set of rules that BAN nodes must adhere to is defined. For example, a rule may require that a lower priority slot cannot preempt a higher priority allocated slot. Any set of rules may be used. In some embodiments, the rules may be predefined. In other embodiments, rules may be dynamically changed. Rules may be stored in storage 1311 for later use.

In accordance with an exemplary embodiment of the present technology, optimal arrangement of the allocation slots may depend on applying the input parameters and set of rules across all allocation slot arrangements. More particularly, optimal arrangement may depend on maximizing a weighted sum function as shown in Equation (1):

$$\{\alpha_n \mid n \in \Psi\} = \arg\max_{\gamma \in \Gamma} WNUM^{\gamma} \quad (1)$$

Where $$WNUM^{\gamma} = \sum_{n \in \Psi} w_n NUM_n^{\gamma}$$

Where $\alpha_n$ is the allocation slot end time of a node n, $\psi$ is the set of all nodes, $\Gamma$ is the set of all arrangements of allocation slots, $\gamma$ is a specific arrangement of allocation slots, and $NUM_n^{\gamma}$ is a Normalized Utility Metric ("NUM") for a connected BAN node n in allocation slot arrangement $\gamma$, and $w_n$ is a weight factor for a node n as discussed above. Operation steps 1203 through 1207 perform this maximization. In some embodiments, rules engine 1313 may be configured to perform this maximization.

Figure 15:
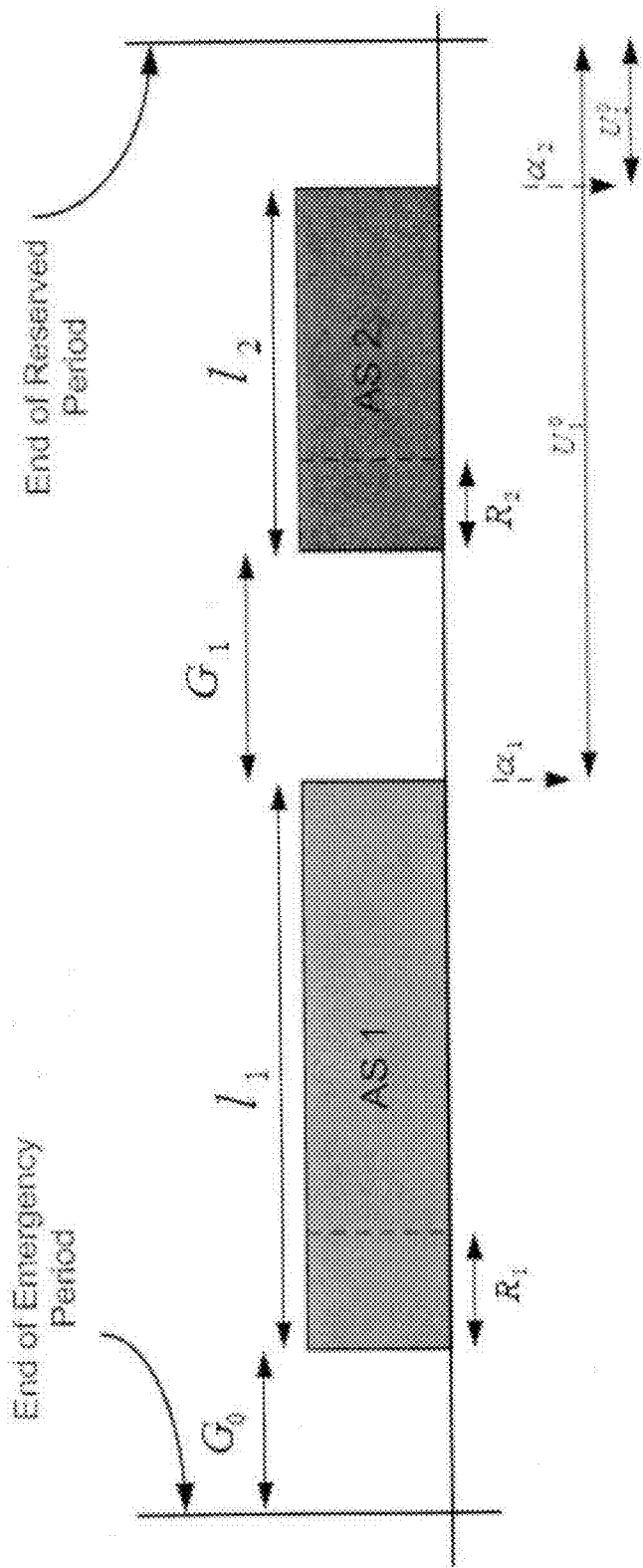
FIG. 15 is an example arrangement and mathematical representation of two allocation slots within a reserved period.

FIG. 15 illustrates an exemplary arrangement of allocation slots under this mathematical framework in accordance with one embodiment of the systems and methods described herein. As described above, the arrangement of allocation slots within a reserved period may be defined as the end times $\alpha_n$ of all nodes ($\alpha_1$ and $\alpha_2$ in FIG. 15). In an alternative embodiment, the optimal arrangement of allocation slots within a reserved period may be defined as the start times of all nodes. An allocation slot may or may not start after the end of a previous allocation slot. Moreover, adjacent allocations slots may have arbitrary gaps. Accordingly, an allocation slot arrangement may be defined as a given order of allocation slots and arbitrary gaps (e.g. $G_0$ and $G_1$ in FIG. 15) between allocation slots or between allocation slots and the reserved period's boundaries.

Returning now to FIGS. 12 and 13, at operation 1203, a Normalized Utility Metric ("NUM") is calculated for a BAN node 1340 in a connected state for an allocation slot arrangement. The NUM represents the expected realizable allocation slot length of the node, normalized by the node's initially scheduled allocation slot length. The expected realizable allocation slot length may depend on factors such as, for example, preemption by other allocation slots, emergency events, and the node consuming more bandwidth than granted. As discussed below, calculation of the NUM may be based on the set of input parameters and rules. At operation 1204, a check is performed for any additional nodes that have not had their NUM calculated for that allocation slot arrangement. If there are additional nodes, additional NUMs are computed. Otherwise, arrangement process 1200 proceeds to operation 1205.

At operation 1205, a weighted NUM sum ("WNUM") for the particular allocation slot arrangement is computed by taking the summation of all weighted NUMs for the allocation slot arrangement. At operation 1206, a check is performed to see for any additional allocation slot arrangements that have not had their WNUM calculated. If there are additional allocation slot arrangements, operations 1203 through 1206 are repeated. Otherwise, arrangement process 1200 proceeds to operation 1207. At operation 1207, the allocation slot arrangement that corresponds to the highest computed WNUM is selected.

With the allocation slot arrangement selected, at operation 1208 the BAN hub may create a schedule message (containing this arrangement) for broadcast (operation 1209) to nodes 1350.

In accordance with an exemplary embodiment of the present technology, a mathematical framework is formulated using Equation (1), the input parameters of FIG. 14 and a specific set of rules. With reference to FIG. 15, let $U_n^x$ denote the distance of a node n's allocation slot's end time $\alpha_n$ from the no pass-zone when its start time is delayed by x seconds. For the formulation illustrated in FIG. 15 (where the no-pass zone is the start of the Unreserved Period) $U_n^0 = L - \alpha_n$ and $U_n^x = U_n^0 - x$. Note that, by way of example, unless otherwise stated the start of the Reserved Period is used as the reference point in time.

Now, by way of example, consider a specific set of rules that BAN nodes adhere to comprise the following four rules:
1) Each node can wake up only once during a Reserved Period;
2) In case an awakened slave is not polled at the predetermined time by the hub, it can keep awake for a maximum of $R_n$.
3) $R_n < l_n$.
4) If node n is polled within time $x < R_n$ of its awakening, it is granted an AS length of $\min(l_n, l_n + U_n^x)$.

The selection of this set of rules is by way of example only, and is not meant to be limiting. In this embodiment, the no-pass zone is the beginning of the Unreserved Period. Yet, the mathematical framework has been designed general enough such that other embodiments could add the rule "A lower priority allocation slot cannot preempt a higher priority allocation slot." Under these alternative embodiments, the no-pass zone would be the negotiated start time of the closest higher priority allocation slot.

In one embodiment, a mathematical framework is shown for a BAN consisting of a hub and two nodes (i.e. n=2, two allocation slots). Before finding $NUM_n^\gamma$, $n \in \psi$, $\gamma \in \Gamma$, define Equation (2):

$$A_n^x = \min(l_n, l_n + U_n^x) + p_n \int_0^{\max(0, U_n^x)} x_n f_{x_n}(x_n) dx_n \quad (2)$$

Where, $A_n^x$ denotes the expected length of node n's allocation slot when its start time is delayed by x seconds. The term containing the integral accounts for the increase in node n's allocation slot length caused by its own (possible) SiGE. From the above, Equations (3) and (4) follow for an exponentially distributed SiGE function $f_{x_n}(x_n)$.

For $U_n^x \geq 0$ $$A_n^x = l_n + p_n \left( \frac{1}{\lambda_n} - e^{-\lambda_n U_n^x} \left( U_n^x + \frac{1}{\lambda_n} \right) \right) \quad (3)$$

For $U_n^x < 0$ $$A_n^x = l_n + U_n^x \quad (4)$$

Because $U_n^0 \geq 0$, $A_n^0$ takes the form of Equation (3). Based on definitions and assumptions, $NUM_1^\gamma$ may be defined by Equation (5):

$$NUM_1^\gamma = \frac{A_1^0}{l_1} \quad (5)$$

Although normalized, NUM may be greater than 1 (e.g. $NUM_1^\gamma$, when the first allocation slot's start time is not delayed and it also performs a SiGE).

$NUM_2^\gamma$ may be defined by Equation (6):

$$NUM_2^\gamma = \frac{1}{l_2}\bigg((1-p_1)A_2^0 + \quad (6)$$
$$p_1 \bigg( \int_0^{G_1} f_{x_1}(x_1) A_2^0 dx_1 + \int_{G_1}^{G_1+R_2} f_{x_1}(x_1) A_2^{x_1} dx_1 \bigg) \bigg) =$$
$$\frac{1}{l_2}\bigg(A_2^0(1 - p_1 e^{-\lambda_1 G_1}) + p_1 \int_{G_1}^{G_1+R_2} f_{x_1}(x_1) A_2^{x_1} dx_1\bigg)$$

Note that if allocation slot 1 does not perform a SIGE or its grant extension length $x_1$ is less than $G_1$, then allocation slot 2 has expected length $A_2^0$. On the other hand, if $G_1 \leq x_1 \leq G_1 + R_2$, then the expected length of allocation slot 2 depends on how much its start time is delayed. For $x_1 > G_1 + R_2$, allocation slot 2 is preempted (corresponding node goes back to sleep without gaining channel access) and its expected allocation slot length is zero.

To compute the integral in Equation (6), account for two cases:

$R_2 < U_2^0$

In this case for $G_1 \leq x_1 \leq G_1 + R_2$, $U_2^{x_1} > 0$ (which means node 2 can at least transmit for the initially scheduled duration) and hence $A_2^{x_1}$ is of the form of Equation (3). Replacing that in Equation (6) and using an exponentially distributed $X_1$, Equation (7) may be derived:

$$NUM_2^\gamma = \frac{A_2^0 + W^T V}{l_2} \quad (7)$$

Where $$W = \begin{bmatrix} -p_i e^{-\lambda_1 R_2}\left(l_2 + \frac{p_2}{\lambda_2}\right) \\ p_1 p_2 e^{-\lambda_2 \bar{l}} \left( \frac{\lambda_i}{\lambda_2 - \lambda_1}((\bar{l}\lambda_1\lambda_2 - G_0 - G_1)(1 - e^{(\lambda_2 - \lambda_1)R_2}) + \\ R_2 e^{(\lambda_2 - \lambda_1)R_2}) + (\bar{l}\lambda_2 - G_0 - G_1)\right) \end{bmatrix}$$

$$V = [\, e^{-\lambda_1 G_1} \quad e^{-\lambda_1 G_1 + \lambda_2(G_0 + G_1)} \,]$$

In which $\bar{l} = L - l_1 - l_2$, $\bar{l}_{\lambda_2} = \frac{1}{\lambda_2}$, and $$\bar{l}_{\lambda_1, \lambda_2} = \bar{l} + \frac{1}{\lambda_2} + \frac{1}{\lambda_2 - \lambda_1} \text{ for } \lambda_1 \neq \lambda_2.$$

$R_2 \geq U_2^0$

In this case $G_1 \leq x_1 \leq G_1 + R_2$ is broken into two subintervals:
1) $G_1 \leq x_1 \leq G_1 + U_2^0$: here $U_2^{x_1} > 0$ and hence $A_2^{x_1}$ takes the form of Equation (3).
2) $G_1 + U_2^0 < x_1 \leq R_2$: here $U_2^{x_1} < 0$ and hence $A_2^{x_1}$ takes the form of Equation (4). Note that in this case node 2 gets an allocation which is less than what it had initially been scheduled for by the BAN Hub. This is due to the shift in its start time which brings it closer to the end of the Reserved Period.

Hence for this case again Equation (7) delivers $NUM_2^\gamma$ but this time (for $\lambda_1 \neq \lambda_2$):

$$W = \begin{bmatrix} p_1 e^{-\lambda_1 R_2}\left(R_2 + \frac{1}{\lambda_1} - l_2 - \bar{l} + G_0 + G_1\right) \\ -p_1 e^{-\lambda_1 \bar{l}}\left(\frac{1}{\lambda_1} + \frac{p_2}{\lambda_2} + \frac{p_2\lambda_1}{\lambda_2-\lambda_1}\left(\frac{1}{\lambda_2} + \frac{1}{\lambda_2-\lambda_1}\right)\right) \\ p_1 p_2 e^{-\lambda_2 \bar{l}}\left(\bar{l}\lambda_2 - G_0 - G_1 + \frac{\lambda_1}{\lambda_2-\lambda_1}(\bar{l}\lambda_1\lambda_2 - G_0 - G_1)\right) \end{bmatrix}$$

$$V = [\, e^{-\lambda_1 G_1} \quad e^{\lambda_1 G_0} \quad e^{-\lambda_1 G_1 + \lambda_2(G_0 + G_1)} \,]$$

Compared to $NUM_1^\gamma$, $NUM_2^\gamma$ has a corrective term $W^T V$ that is a function of the statistical characteristics of SiGEs, negotiated allocation slot lengths, and the parameters of allocate slot arrangement $\gamma$, i.e. gap values $G_0$ and $G_1$. This may account for the reduction in allocation slot 2's expected length because of allocation slot 1's probable SiGE and also less time for its own preemption due to the delay in its start time.

Values of $NUM_1^\gamma$ and $NUM_2^\gamma$ can now be replaced in Equation (1) to achieve $WNUM^\gamma$ for a given arrangement of allocation slots, i.e. for a given $G_0$ and $G_1$. Since WNUM is a concave function of $G_0$ and $G_1$, their optimal values can be recovered (for a given permutation of allocation slots) using optimization methods.

Figure 16:
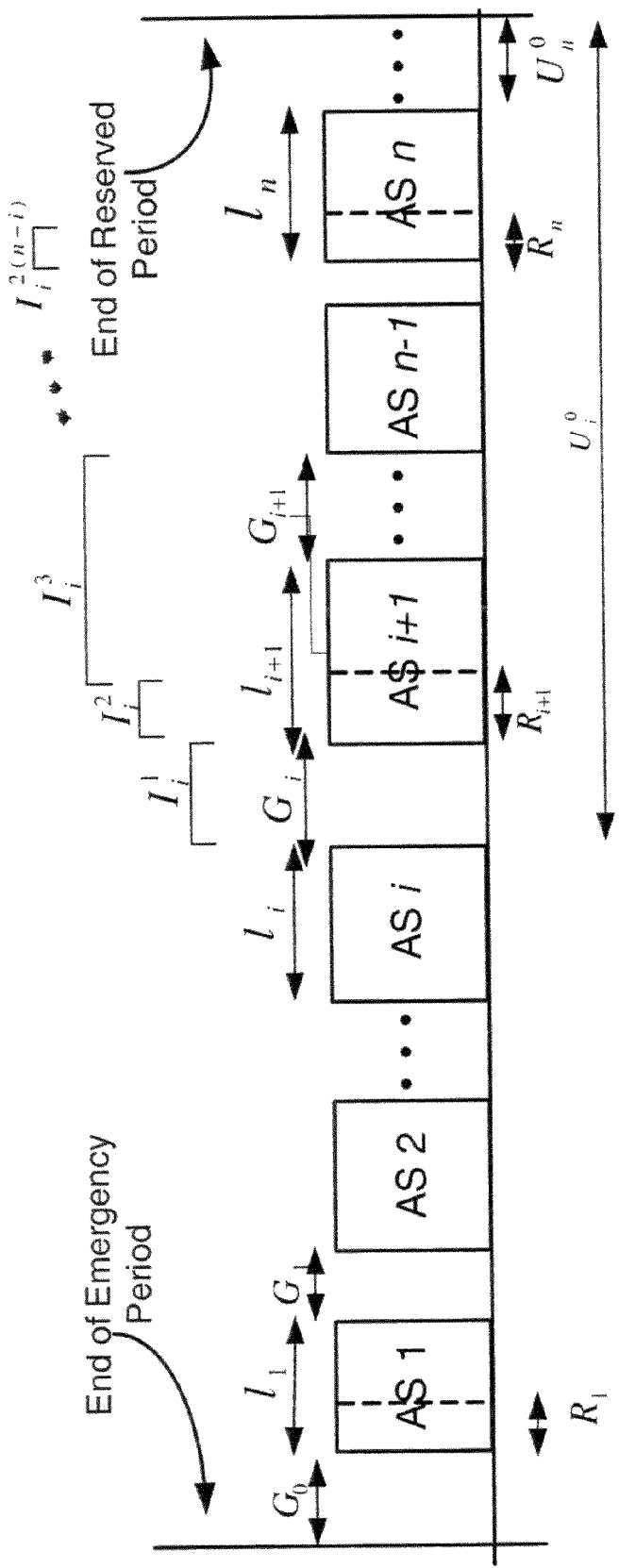
FIG. 16 is an example arrangement and mathematical representation of n allocation slots within a reserved period.

In another embodiment, a mathematical framework is shown for a BAN comprising a hub and an arbitrary number of n nodes. This framework may be based on a generalization of the two-node framework discussed above. In accordance with the present embodiment, FIG. 16 illustrates an arrangement of n allocation slots in accordance with one embodiment of the systems and methods described herein. To find an optimal allocation slot arrangement, for arbitrary n for $NUM_n^\gamma$, $n \in \psi$, $\gamma \in \Gamma$ Equation (8) may be derived:

$$l_n NUM_n^\gamma = \prod_{j=0}^{n-1}(1-p_j)A_n^0 + \sum_{i=0}^{n-1}\prod_{j=0}^{i-1}(1-p_j)p_i A_n(x_i, \ldots, x_{n-1}) \quad (8)$$

Where the first summand accounts for the case where none of the allocation slots before allocation slot n have grant extensions and where no emergency event is happening. Here, $$NUM_n^\gamma = \frac{A_n^0}{l_n}$$

as allocation slot n's start time is not delayed. The terms inside the summation account for the case where there is either an emergency happening or when node i, for $1 \leq i < n$, (and none of the allocation slots before node i) is having a grant extension.

$A_n(x_i, \ldots, x_{n-1})$ denotes the expected length of node n's allocation slot upon node i's SiGE, where node n's allocation start time can be affected by $x_i, \ldots, x_{n-1}$. Finding $NUM_n^\gamma$ depends on finding $A_n(x_i, \ldots, x_{n-1})$, $1 \leq i < n$.

Define the intervals (see FIG. 16) as shown below:

$$l_i^1 = [0, G_i], l_i^2 = [G_i, G_i + R_{i+1}], l_i^3 = [G_i + R_{i+1}, G_i + l_{i+1} + G_{i+1}], \ldots, l_i^{2(n-i)} = [G_i + \Sigma_{j=i+1}^{n-1} G_j + l_j R_n + G_i + \Sigma_{j=i+1}^{n-1} G_j + l_j]$$

For these intervals, when $1 \leq i < n$ the reference time is the scheduled end time of node i's allocation slot. For $i=0$, i.e. for emergency events, the reference time is the beginning of the Reserved Period.

Accordingly, using the law of total probability Equation (9) may be derived:

$$A_n(x_i, \ldots, x_{n-1}) = \sum_{k=1}^{2(n-i)} \int_{J_i^k} f_{X_i}(x_i) A_n(X_i = x_i, \ldots, x_{n-1}) dx_i \quad (9)$$

Where $A_n(X_i=x_i, \ldots, x_{n-1})$ is $A_n(x_i, \ldots, x_{n-1})$ conditional on the event $\{X_i=x_i\}$. Finding $A_n(X_i=x_i, \ldots, x_{n-1})$ over each of the predefined intervals leads to the solution. As an example, assume $i=n-2$, $x_i \in I_i^2$ i.e. $G_{n-2} \leq x_{n-2} < G_{n-2} + R_{n-1}$.

Figure 17:
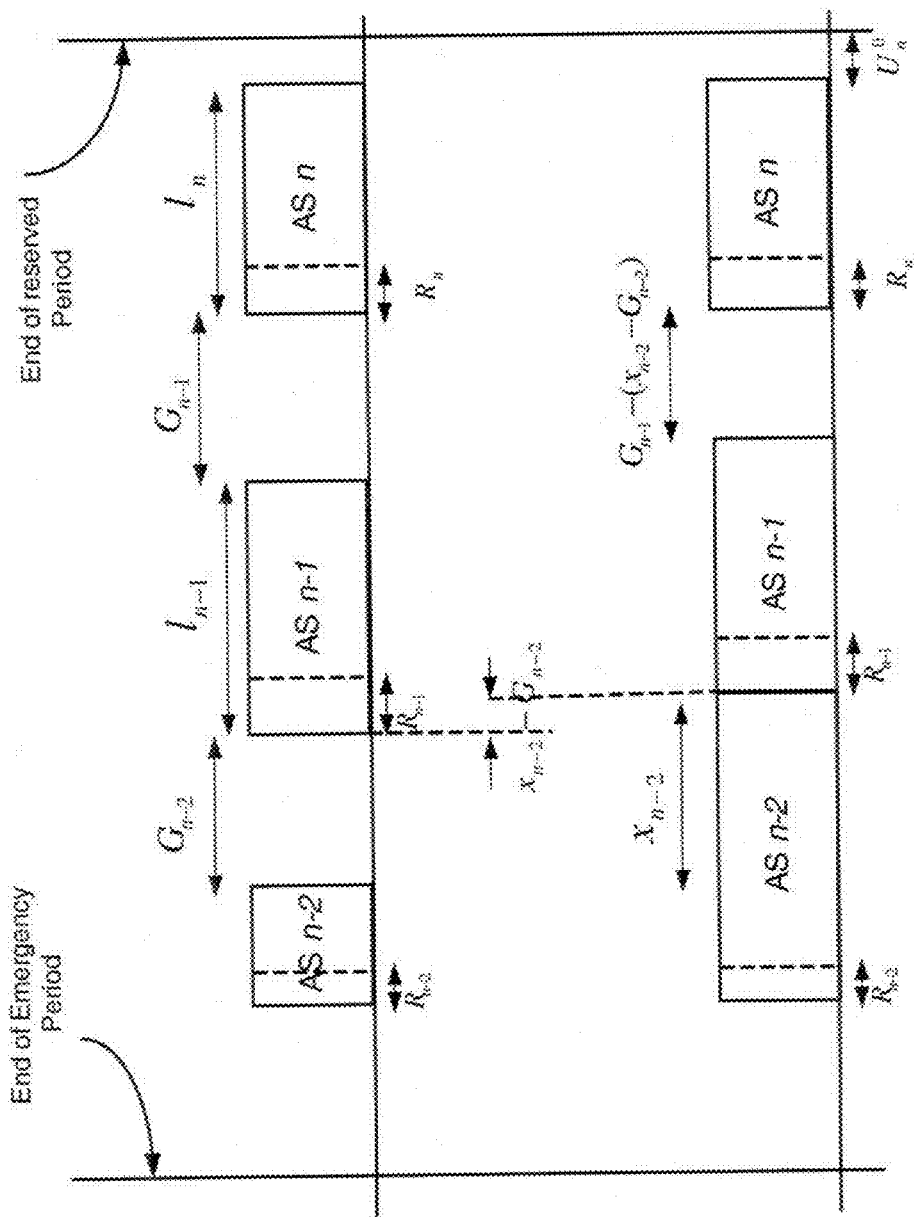
FIG. 17 is an example arrangement and mathematical representation of an allocation slot before and after a Sensor-initiated Grant Extension. The dashed region shows the length of the Sensor-initiated Grant Extension.

FIG. 17 illustrates this example scenario. The dashed region for allocation slot n−2 shows the grant extension length. This grant extension causes the start time of allocation slot n−1 to be shifted by $x_{n-2} - G_{n-2}$.

For $R_{n-1} \leq G_{n-1}$, $G_{n-1} - (x_{n-2} - G_{n-2}) \geq 0$.

Accordingly:

$$A_n(X_{n-2} = x_{n-2}, x_{n-1}) = (1 - p_{n-1})$$
$$A_n^0 + p_{n-1}\left(A_n^0 \int_0^{G_{n-1}+G_{n-2}-x_{n-2}} f_{X_{n-1}}(x_{n-1}) dx_{n-1} + \right.$$
$$\left. \int_{G_{n-1}+G_{n-2}-x_{n-2}}^{R_n+G_{n-1}+G_{n-2}-x_{n-2}} f_{X_{n-1}}(x_{n-1}) A_n(X_{n-2}=x_{n-2}, X_{n-1}=x_{n-1}) dx_{n-1}\right)$$

Where for $R_n \leq U_n^0$, $A_n(X_{n-2}=x_{n-2}, X_{n-1}=x_{n-1})$ takes the form of Equation (3) but with:

$$U_n^{x_{n-2},x_{n-1}} = U_n^0 + G_{-2} + G_{n-1} - x_{n-2} - x_{n-1}$$

$A_n(x_i, \ldots, x_{n-1})$ for other values of $1 \leq i < n$ may similarly be found and replaced in Equation (8) to yield the result for $NUM_n^\gamma$ which is then used in the optimization framework of Equation (1).

Figure 18:
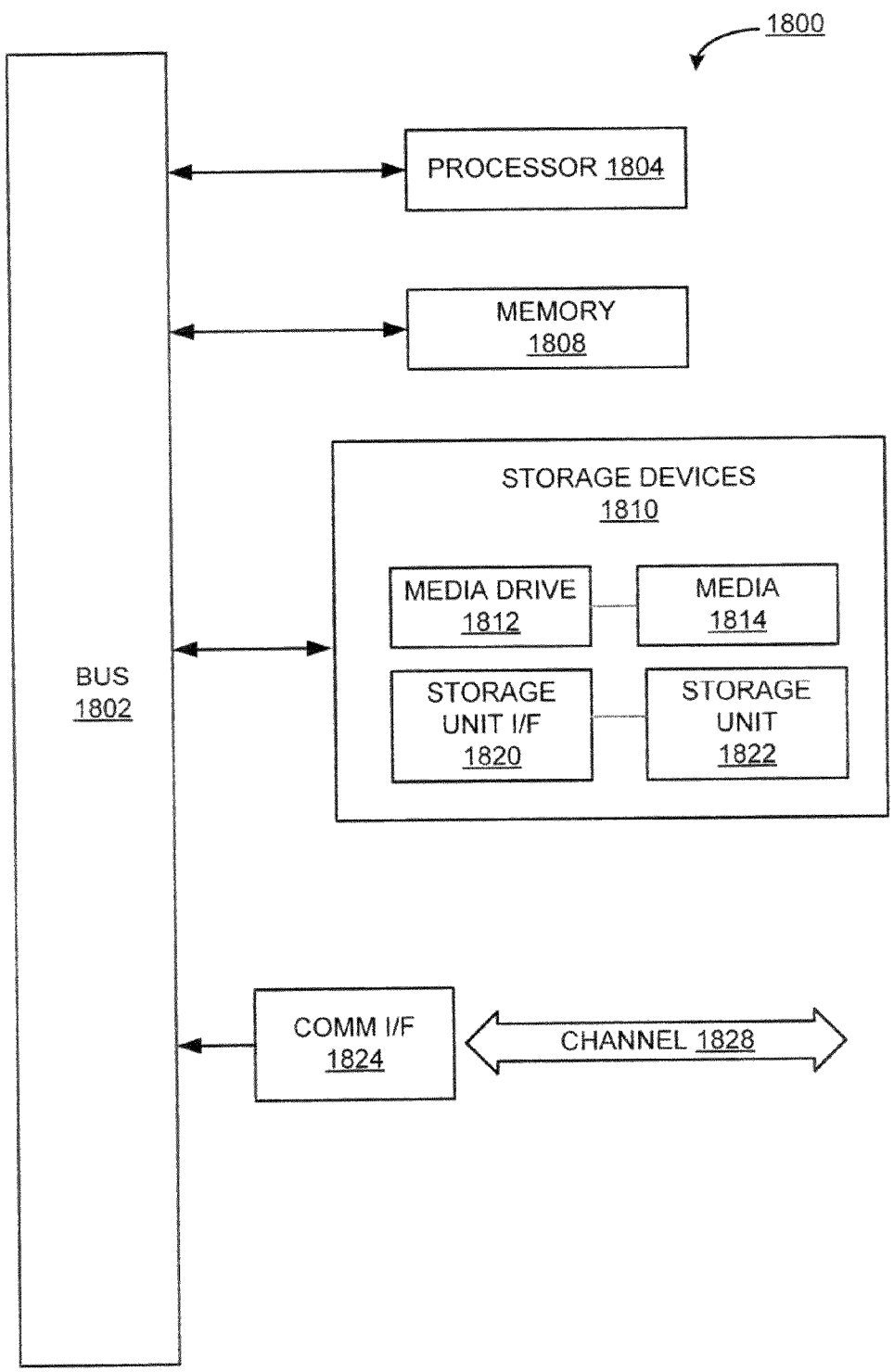
FIG. 18 illustrates an example computing module that may be used in implementing various features of embodiments of the disclosed technology.

As used herein, the term module might describe a given unit of functionality that can be performed in accordance with one or more embodiments of the technology disclosed herein. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the technology are implemented in whole or in part using software, in one embodiment, these software elements can be implemented to operate with a computing or processing module capable of carrying out the functionality described with respect thereto. One such example computing module is shown in FIG. 18. Various embodiments are described in terms of this example-computing module 1800. After reading this description, it will become apparent to a person skilled in the relevant art how to implement the technology using other computing modules or architectures.

Referring now to FIG. 18, computing module 1800 may represent, for example, computing or processing capabilities found within desktop, laptop and notebook computers; handheld computing devices (PDA's, smart phones, cell phones, palmtops, etc.); mainframes, supercomputers, workstations or servers; or any other type of special-purpose or general-purpose computing devices as may be desirable or appropriate for a given application or environment. Computing module 1800 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 1800 might include, for example, one or more processors, controllers, control modules, or other processing devices, such as a processor 1804. Processor 1804 might be implemented using a general-purpose or special-purpose processing engine such as, for example, a microprocessor, controller, or other control logic. In the illustrated example, processor 1804 is connected to a bus 1802, although any communication medium can be used to facilitate interaction with other components of computing module 1800 or to communicate externally.

Computing module 1800 might also include one or more memory modules, simply referred to herein as main memory 1808. For example, preferably random access memory (RAM) or other dynamic memory, might be used for storing information and instructions to be executed by processor 1804. Main memory 1808 might also be used for storing temporary variables or other intermediate information during execution of instructions to be executed by processor 1804. Computing module 1800 might likewise include a read only memory ("ROM") or other static storage device coupled to bus 1802 for storing static information and instructions for processor 1804.

The computing module 1800 might also include one or more various forms of information storage mechanism 1810, which might include, for example, a media drive 1812 and a storage unit interface 1820. The media drive 1812 might include a drive or other mechanism to support fixed or removable storage media 1814. For example, a hard disk drive, a floppy disk drive, a magnetic tape drive, an optical disk drive, a CD or DVD drive (R or RW), or other removable or fixed media drive might be provided. Accordingly, storage media 1814 might include, for example, a hard disk, a floppy disk, magnetic tape, cartridge, optical disk, a CD or DVD, or other fixed or removable medium that is read by, written to or accessed by media drive 1812. As these examples illustrate, the storage media 1814 can include a computer usable storage medium having stored therein computer software or data.

In alternative embodiments, information storage mechanism 1810 might include other similar instrumentalities for allowing computer programs or other instructions or data to be loaded into computing module 1800. Such instrumentalities might include, for example, a fixed or removable storage unit 1822 and an interface 1820. Examples of such storage units 1822 and interfaces 1820 can include a program cartridge and cartridge interface, a removable memory (for example, a flash memory or other removable memory module) and memory slot, a PCMCIA slot and card, and other fixed or removable storage units 1822 and interfaces 1820 that allow software and data to be transferred from the storage unit 1822 to computing module 1800.

Computing module 1800 might also include a communications interface 1824. Communications interface 1824 might be used to allow software and data to be transferred between computing module 1800 and external devices. Examples of communications interface 1824 might include a modem or softmodem, a network interface (such as an Ethernet, network interface card, WiMedia, IEEE 1802.XX or other interface), a communications port (such as for example, a USB port, IR port, RS232 port Bluetooth® interface, or other port), or other communications interface. Software and data transferred via communications interface 1824 might typically be carried on signals, which can be electronic, electromagnetic (which includes optical) or other signals capable of being exchanged by a given communications interface 1824. These signals might be provided to communications interface 1824 via a channel 1828. This channel 1828 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 1808, storage unit 1820, media 1814, and channel 1828. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 1800 to perform features or functions of the disclosed technology as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A method of arranging a plurality of allocation slots, wherein each of the plurality of allocation slots has been allocated to a respective one of a plurality of nodes in a body area network (BAN), the method comprising:
receiving at a BAN hub a set of input parameters corresponding to the plurality of nodes, wherein the input parameters comprise a Sensor-initiated Grant extension (SIGE) probability and a SIGE length distribution of one of the plurality of nodes, wherein the SIGE is an extension of an allocation slot duration beyond a granted allocation slot duration;
setting rules that each of the plurality of nodes must follow in the BAN network; and
selecting an allocation slot arrangement of the plurality of allocation slots based on the input parameters and the rules, wherein the BAN hub selects the allocation slot arrangement.

2. The method of claim 1 wherein selecting the allocation slot arrangement based on the input parameters and the rules further comprises:
calculating a normalized utility metric for each of the plurality of nodes for the allocation slot arrangement, wherein the normalized utility metric represents the expected realizable allocation slot length of a node, normalized by its initially scheduled allocation slot length;
computing a weighted sum for the allocation slot arrangement based on the calculated utility metrics; and
selecting the allocation slot arrangement if the computed weighted sum maximizes a weighted sum function.

3. The method of claim 2 wherein the calculation of the normalized utility metric for each of the plurality of nodes in the allocation slot arrangement is based on the rules and the input parameters.

4. The method of claim 3 wherein the allocation slot arrangement comprises the order of the allocation slots, any gaps between the allocation slots, and any gaps between the allocation slots and boundaries of a reserved period for the allocation slots.

5. The method of claim 4 wherein the input parameters comprise a maximum length of the reserved period, emergency event parameters, and characteristics of each of the plurality of nodes.

6. The method of claim 5 wherein the input parameters comprise a weight factor of each of the plurality of nodes.

7. The method of claim 6 wherein the weight factor of each of the plurality of nodes is based on the node's respective Quality of Service ("QOS") latency and reliability requirements.

8. The method of claim 1 wherein the input parameters comprise a scheduled allocation slot length, a reschedule tolerance threshold, a SIGE probability, and a SIGE length distribution of each of the plurality of nodes.

9. The method of claim 2 wherein the weighted sum function comprises a plurality of weighted sums calculated for each of a plurality of allocation slot arrangements.

10. The method of claim 6 wherein the weighted sum function comprises the plurality of weight factors corresponding to each of the plurality of nodes.

11. The method of claim 4 wherein the rules comprise the requirement that a node can wake up only once during a reserved period.

12. The method of claim 1 wherein the rules comprise at least one of the following requirements:
if an awakened node is not polled at the start of its allocated slot by the BAN hub, the awakened node may keep awake for a maximum of the awakened node's reschedule tolerance threshold;
a node's reschedule tolerance threshold ($R_n$) is less than its scheduled allocation slot length ($l_n$); and
if a node is polled within $x < R_n$, of it awakening, the polled node is granted an allocation slot length of min($l_n$, $l_n + U_n^x$, wherein $U_n^x$ is the distance of the polled node's allocation slot end time from a no pass zone when its start time is delayed by x positive seconds, wherein the no pass zone is a beginning of an unreserved period.

13. The method of claim 4, further comprising the BAN hub broadcasting to the plurality of nodes a message containing the selected allocation slot arrangement.

14. The method of claim 12 wherein the rules comprise the requirement that if a node is polled within $x < R_n$ of it awakening, the polled node is granted an allocation slot length of $\min(l_n, l_n+U_n^x)$, wherein $U_n^x$ is the distance of the polled node's allocation slot end time from a no pass zone when its start time is delayed by x positive seconds, wherein the no pass zone is a beginning of an unreserved period.

15. A network device configured to perform a method of arranging a plurality of allocation slots, wherein each of the plurality of allocation slots has been allocated to a respective one of a plurality of nodes in a body area network (BAN), the network device comprising:
  one or more processors;
  one or more non-transitory computer-readable mediums operatively coupled to at least one of the one or more processors and having instructions stored thereon that, when executed by at least one of the one or more processors, cause at least one of the one or more processors to:
  receive a set of input parameters corresponding to the plurality of nodes, wherein the input parameters comprise a Sensor-initiated Grant extension (SIGE) probability and a SIGE length distribution of one of the plurality of nodes, wherein the SIGE is an extension of an allocation slot duration beyond a granted allocation slot duration;
  set rules that each of the plurality of nodes must follow in the BAN network; and
  select an allocation slot arrangement of the plurality of allocation slots based on the input parameters and the rules.

16. The network device of claim 15, wherein selecting the allocation slot arrangement based on the input parameters and the rules further comprises:
  calculating a normalized utility metric for each of the plurality of nodes for the allocation slot arrangement, wherein the normalized utility metric represents the expected realizable allocation slot length of a node, normalized by its initially scheduled allocation slot length;
  computing a weighted sum for the allocation slot arrangement based on the calculated utility metrics; and
  selecting the allocation slot arrangement if the computed weighted sum maximizes a weighted sum function.

17. The network device of claim 16 wherein the calculation of the normalized utility metric for each of the plurality of nodes in the allocation slot arrangement is based on the rules and the input parameters.

18. The network device of claim 17 wherein the allocation slot arrangement comprises the order of the allocation slots, any gaps between the allocation slots, and any gaps between the allocation slots and boundaries of a reserved period for the allocation slots.

19. The network device of claim 18 wherein the input parameters comprise a maximum length of the reserved period, emergency event parameters, and characteristics of each of the plurality of nodes.

20. The network device of claim 19 wherein the input parameters comprise a weight factor of each of the plurality of nodes.

21. The network device of claim 20 wherein the weight factor of each of the plurality of nodes is based on the node's respective Quality of Service ("QOS") latency and reliability requirements.

22. The network device of claim 15 wherein the input parameters comprise a scheduled allocation slot length, a reschedule tolerance threshold, a SIGE probability, and a SIGE length distribution of each of the plurality of nodes.

23. The network device of claim 16 wherein the weighted sum function comprises a plurality of weighted sums calculated for each of a plurality of allocation slot arrangements.

24. The network device of claim 20 wherein the weighted sum function comprises the plurality of weight factors corresponding to each of the plurality of nodes.

25. The network device of claim 18 wherein the rules comprise the requirement that a node can wake up only once during a reserved period.

26. The network device of claim 15 wherein the rules comprise at least one of the following requirements:
  if an awakened node is not polled at the start of its allocated slot by the BAN hub, the awakened node may keep awake for a maximum of the awakened node's reschedule tolerance threshold;
  a node's reschedule tolerance threshold ($R_n$) is less than its scheduled allocation slot length ($l_n$); and
  if a node is polled within $x < R_n$, of it awakening, the polled node is granted an allocation slot length of $\min(l_n, l_n+U_n^x)$, wherein $U_n^x$ is the distance of the polled node's allocation slot end time from a no pass zone when its start time is delayed by x positive seconds, wherein the no pass zone is a beginning of an unreserved period.

27. The network device of claim 18, further comprising a transceiver configured to broadcast to the plurality of nodes a message containing the allocation slot arrangement.

28. The network device of claim 26 wherein the rules comprise the requirement that if a node is polled within $x < R_n$ of it awakening, the polled node is granted an allocation slot length of $\min(l_n, l_n+U_n^x)$, wherein $U_n^x$ is the distance of the polled node's allocation slot end time from a no pass zone when its start time is delayed by x positive seconds, wherein the no pass zone is a beginning of an unreserved period.

29. The network device of claim 18, wherein the network device is a BAN hub.

* * * * *